US011008295B2

(12) United States Patent
Hernández Cabanillas et al.

(10) Patent No.: US 11,008,295 B2
(45) Date of Patent: May 18, 2021

(54) COMPOUNDS HAVING ANTIINFECTIVE, ANTITUMORAL AND ANTIFUNGAL ACTIVITY

(71) Applicant: HORITZONTS TECNOLOGICS HUNGARY KORLÁTOLT FELELOSSÉGU TÁRSASÁG, Budapest (HU)

(72) Inventors: Alfredo Hernández Cabanillas, Cáceres (ES); Santiago Maderuelo Corral, Madrid (ES); Montserrat Ortega Doménech, Madrid (ES); Diego Fernando Rosero Valencia, Madrid (ES); Ángel Rumbero Sánchez, Madrid (ES); Victor Tena Pérez, Villanueva de la Serena (ES)

(73) Assignee: HORITZONTS TECNOLOGICS HUNGARY KORLÁTOLT FELELOSSÉGU TÁRSASÁG, Budapest (HU)

( * ) Notice: Subject to any disclaimer, the term of this patent is extended or adjusted under 35 U.S.C. 154(b) by 0 days.

(21) Appl. No.: 16/608,268

(22) PCT Filed: Apr. 25, 2018

(86) PCT No.: PCT/EP2018/060518
§ 371 (c)(1),
(2) Date: Oct. 25, 2019

(87) PCT Pub. No.: WO2018/197523
PCT Pub. Date: Nov. 1, 2018

(65) Prior Publication Data
US 2020/0190044 A1 Jun. 18, 2020

(30) Foreign Application Priority Data
Apr. 26, 2017 (EP) .................... 17382224

(51) Int. Cl.
*C07D 273/04* (2006.01)
*A61P 31/22* (2006.01)
*A61P 31/18* (2006.01)
*A61P 31/10* (2006.01)
*A61P 35/00* (2006.01)

(52) U.S. Cl.
CPC ............ *C07D 273/04* (2013.01); *A61P 31/10* (2018.01); *A61P 31/18* (2018.01); *A61P 31/22* (2018.01); *A61P 35/00* (2018.01)

(58) Field of Classification Search
CPC .................................................. C07D 273/04
USPC ...................................................... 514/229.2
See application file for complete search history.

(56) References Cited

FOREIGN PATENT DOCUMENTS

EP 3 156 400 A1 5/2016

OTHER PUBLICATIONS

Garcia-Perez, J. et al., "A New Strategy Based on Recombinant Viruses as a Tool for Assessing Drug Susceptibility of Human Immunodeficiency Virus Type 1", Journal of Medical Virology, vol. 79, 2007, pp. 127-137.
Ke, S. et al., "Synthesis and Biological Properties of Dihydro-Oxadiazine-Based Heterocyclic Derivatives", Mini-Reviews in Medicinal Chemistry, vol. 11, 2011, pp. 642-657.
Rathbone, M.J. et al., "Modified-Release Drug Delivery Technology", Marcel Dekker Inc., 2002, pp. 589-598.

*Primary Examiner* — Kahsay Habte
(74) *Attorney, Agent, or Firm* — Gary J. Gershik; Cooper & Dunham LLP

(57) ABSTRACT

The invention relates to novel compounds and their use in medicine, particularly in treating and/or preventing infections caused by a bacterium, fungus or virus or in treating and/or preventing cancer. Additionally, the invention relates to a process for obtaining the compounds of the invention.

19 Claims, 7 Drawing Sheets

COMPOUNDS HAVING ANTIINFECTIVE, ANTITUMORAL AND ANTIFUNGAL ACTIVITY

RELATED APPLICATIONS

This application is a § 371 national stage of PCT International Application No. PCT/EP2018/060518, filed Apr. 25, 2018, claiming priority of European Patent Application No. 17382224.8, filed Apr. 26, 2017, the contents of each of which are hereby incorporated by reference into this application.

TECHNICAL FIELD OF INVENTION

The present invention relates to process for preparing new compounds and their use in medicine.

BACKGROUND OF INVENTION

The discovery of penicillin ushered in the "antibiotic era" and the ability to cure infections which were previously often fatal.

The advantages offered by antibiotics in the treatment of infectious diseases are compromised due to the increase in the number of antibiotic-resistant bacterial strains. Antimicrobial resistance makes it difficult and more expensive to treat common infections, causing delays in effective treatment, or in worst cases, inability to provide appropriate therapy. The predictable consequences of resistance are increased morbidity, prolonged illness, a greater risk of complications, and higher mortality rates. The economic burden includes loss of productivity (loss in income, diminished worker productivity, time spent by family) and increased cost of diagnostics and treatment (consultation, infrastructure, screening, cost of equipment, drugs . . . ). It has been reported that every year 25000 patients die in the European Union from a bacterial infection which is multi-resistant to the presently existing drugs.

The problem of resistance also covers the major pathogenic fungi and yeasts, encompassing fungal infections, with ever increasing due to their behavior as typical opportunistic. To date, fungal infections continue to be an important cause of morbidity and very high mortality, and may reach up to 100% in some disseminated infections.

Furthermore, cancers have the ability to develop resistance to traditional therapies, and the increasing prevalence of these drug resistant cancers necessitates further research and treatment development. Resistance to treatment with anticancer drugs results from a variety of factors including individual variations in patients and somatic cell genetic differences in tumors, even those from the same tissue of origin.

In addition, although already exists in the market more than 20 anti-HIV drugs, there is a need of new types of antiviral drugs to palliate the new resistances.

The requirements for new antibiotic, antifungal, antitumor and antiviral molecules are in accordance with current problem of drug and multidrug resistance. It is an increasingly serious threat to global public health that drug resistance is present in all parts of the world. There are now very few effective drugs available to treat recently emerged multidrug resistant infections. Urges the development of new drugs and in this sense, natural products have been a rich source of them for many decades.

Heterocyclic compounds display extensive biological activities, which constitute an important class of natural and synthetic products and are extremely versatile building blocks for the manufacture of bioactive compounds in pharmaceutical drug design and agrochemical industry.

Among them, especially those that are six-membered heterocycles being dihydro-oxadiazine skeleton arouse many research interests, which have been demonstrated to be important heterocyclic scaffold platform with bioactive diversity, which present activities such as cardiovascular, antitumor, antibacterial, antimicrobial, acaricidal, insecticidal, plant-growth regulation, chitin biosynthesis inhibitors and monoamine oxidase inhibition (Ke S. et al., Mini Reviews in Medicinal Chemistry, 2011, 642-657).

There is still a need in the state of the art to identify suitable, effective new compounds for the prevention and/or treatment of infections and cancer.

SUMMARY OF THE INVENTION

In a first aspect, the invention relates to a compound of formula (I):

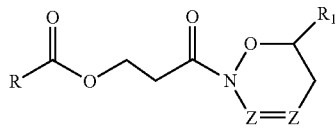

or a pharmaceutically acceptable salt, stereoisomer or solvate thereof,
wherein one Z is N and the other is —C—$R_2$; and $R_2$ and $R_1$ are independently selected from the group consisting of H, alkyl and aryl, and
wherein R is selected from a group consisting of
a) a linear or branched $C_{1-8}$ alkyl, a linear or branched $C_{2-8}$ alkenyl, di-halo methyl, tri-halo methyl, $C_{5-6}$ cycloalkyl, ($C_{1-6}$ alkyl)OCH$_2$—, amine di-substituted with $C_{1-6}$ alkyl groups independently selected,
b) phenyl optionally substituted with one or more groups independently selected from $C_{1-8}$ alkyl, $C_{2-8}$ alkenyl, halogen, phenyl, $C_{1-6}$ alkoxy, amine di-substituted with $C_{1-6}$ alkyl groups independently selected, —NHC(O)$R_3$—, —C(O)NH—$R_3$, —OC(O)$R_3$, and —C(O)O$R_3$—, wherein $R_3$ is $C_{1-6}$ alkyl,
c) 5-6 membered aromatic ring having one or more heteroatoms selected from N, S, and O and being optionally substituted with one or more groups independently selected from:
  $C_{1-8}$ alkyl, linear or branched $C_{2-8}$ alkenyl, $C_{5-6}$ cycloalkyl,
  phenyl as defined in b),
  5-6 membered aromatic ring group,
  halogen,
  ($C_{1-6}$alkyl)OCH$_2$—, $C_{1-6}$ alkoxy,
  amino di-substituted with $C_{1-6}$ alkyl groups,
  NHC(O)$R_3$—, —C(O)NH—$R_3$, —OC(O)$R_3$, and —C(O)O$R_3$—, wherein $R_3$ is $C_{1-6}$ alkyl
d) bicyclic ring containing at least one phenyl group and a $C_{5-6}$ aromatic heterocyclic group having one or more heteroatoms selected from N, S, and O, wherein the phenyl group of said bicyclic ring is optionally substituted with one or more groups independently selected from
  $C_{1-8}$ alkyl, linear or branched $C_{2-8}$ alkenyl, $C_{5-6}$ cycloalkyl,
  phenyl as defined in b),
  5-6 membered aromatic ring group,
  halogen, ($C_{1-6}$alkyl)$OCH_2$—, $C_{1-6}$alkoxy,
amino di-substituted with $C_{1-6}$alkyl groups,
$NHC(O)R_3$—, —$C(O)NH$—$R_3$, —$OC(O)R_3$, and —$C(O)OR_3$—, wherein $R_3$ is $C_{1-6}$ alkyl, and
e) —$CH(R_4)$—$CH(R_5)COOH$, wherein $R_4$ is selected from H, $NH_2$, OH and $CH_2COOH$, and wherein $R_5$ is selected from H, $NH_2$, OH and $CH_2COOH$.

In a second aspect, the invention relates to a method for preparing a compound of formula (I) as defined above, or a pharmaceutically acceptable salt, stereoisomer or solvate thereof, said process comprising reacting a compound of formula (X) in the presence of triethylamine and an organic solvent:

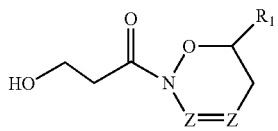
(X)

wherein one Z is N and the other is —C—$R_2$; and $R_2$ and $R_1$ are independently selected from the group consisting of H, alkyl and aryl,
with a compound of formula (XI)

(XI)

wherein X is an halogen or —(O)C(O)R, wherein R is selected from a group consisting of
a) a linear or branched $C_{1-8}$ alkyl, a linear or branched $C_{2-8}$ alkenyl, di-halo methyl, tri-halo methyl, $C_{5-6}$ cycloalkyl, ($C_{1-6}$ alkyl)$OCH_2$—, amine di-substituted with $C_{1-6}$ alkyl groups independently selected,
b) phenyl optionally substituted with one or more groups independently selected from $C_{1-8}$ alkyl, $C_{2-8}$ alkenyl, halogen, phenyl, $C_{1-6}$ alkoxy, amine di-substituted with $C_{1-6}$ alkyl groups independently selected, —$NHC(O)R_3$—, —$C(O)NH$—$R_3$, —$OC(O)R_3$, and —$C(O)OR_3$—, wherein $R_3$ is $C_{1-6}$ alkyl,
c) 5-6 membered aromatic ring having one or more heteroatoms selected from N, S, and O and being optionally substituted with one or more groups independently selected from:
$C_{1-8}$ alkyl, linear or branched $C_{2-8}$ alkenyl, $C_{5-6}$ cycloalkyl,
phenyl as defined in b),
5-6 membered aromatic ring group,
halogen,
($C_{1-6}$alkyl)$OCH_2$—, $C_{1-6}$alkoxy,
amine di-substituted with $C_{1-6}$ alkyl groups,
$NHC(O)R_3$—, —$C(O)NH$—$R_3$, —$OC(O)R_3$, and —$C(O)OR_3$—, wherein $R_3$ is $C_{1-6}$ alkyl
d) bicyclic ring containing at least one phenyl group and a $C_{5-6}$ aromatic heterocyclic group having one or more heteroatoms selected from N, S, and O, wherein the phenyl group of said bicyclic ring is optionally substituted with one or more groups independently selected from
$C_{1-8}$ alkyl, linear or branched $C_{2-8}$ cycloalkyl,
phenyl as defined in b),
5-6 membered aromatic ring group,
halogen,
($C_{1-6}$alkyl)$OCH_2$—, $C_{1-6}$ alkoxy,
amino di-substituted with $C_{1-6}$ alkyl groups,
$NHC(O)R_3$—, —$C(O)NH$—$R_3$, —$OC(O)R_3$, and —$C(O)OR_3$—, wherein $R_3$ is $C_{1-6}$ alkyl, and
e) —$CH(R_4)$—$CH(R_5)$ COOH, wherein $R_4$ is selected from H, $NH_2$, OH and $CH_2COOH$, and wherein $R_5$ is selected from H, $NH_2$, OH and $CH_2COOH$,
or reacting the compound of formula (X) with a compound of formula (XII):

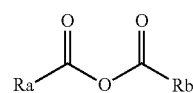
(XII)

wherein Ra and Rb together form, with the anhydride group C(O)OC(O) to which they are attached, a substituted or unsubstituted cyclic group.

In a third aspect, the invention relates to a pharmaceutical composition comprising a compound according to the invention and a pharmaceutically acceptable excipient.

In a fourth aspect, the invention relates to a compound according to the invention or the pharmaceutical composition according to the invention for use in medicine.

In a fifth aspect, the invention relates to a compound or the pharmaceutical composition according to the invention for use in preventing and/or treating an infection caused by a bacterium, fungus or virus or for use in preventing and/or treating cancer.

DETAILED DESCRIPTION OF THE INVENTION

Figure 1:
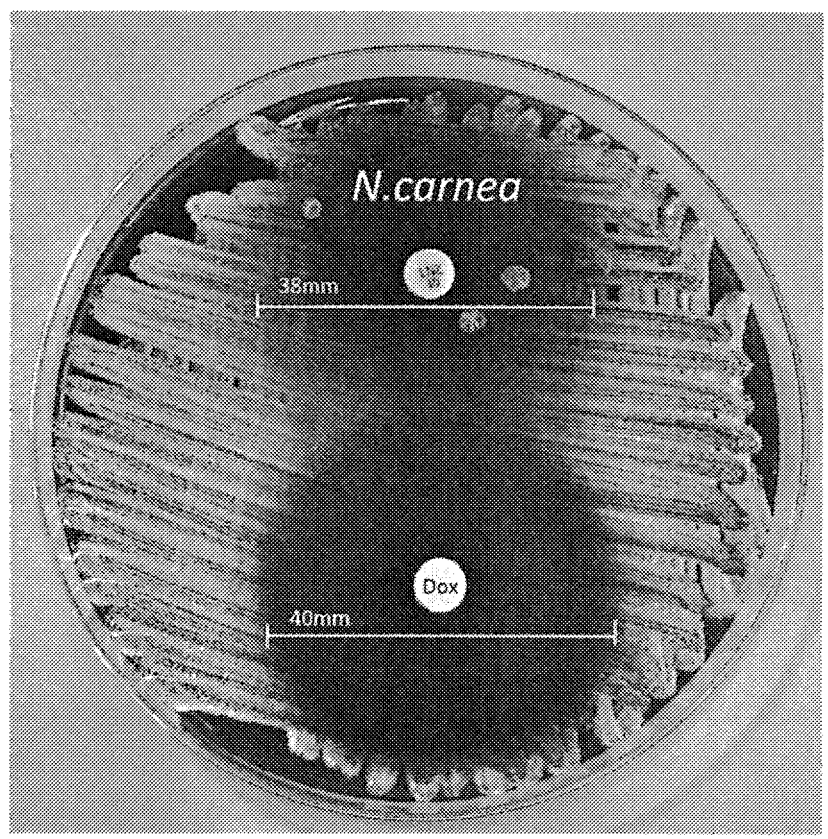
FIG. 1. Activity of the compound doxa 1 in *Nocardia carnea*.

The inventors have identified new compounds having antibiotic, antifungal, antiviral and antitumor activity as shown in Examples 1-5.

Compound

In a first aspect, the invention relates to a compound of formula (I):

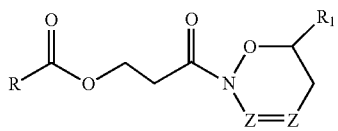

or a pharmaceutically acceptable salt, stereoisomer or solvate thereof,
wherein one Z is N and the other is —C—R$_2$; and R$_2$ and R$_1$ are independently selected from the group consisting of H, alkyl and aryl, and
wherein R is selected from a group consisting of
a) a linear or branched C$_{1-8}$ alkyl, a linear or branched C$_{2-8}$ alkenyl, di-halo methyl, tri-halo methyl, C$_{5-6}$ cycloalkyl, (C$_{1-6}$ alkyl)OCH$_2$—, amine di-substituted with C$_{1-6}$ alkyl groups independently selected,
b) phenyl optionally substituted with one or more groups independently selected from C$_{1-8}$ alkyl, C$_{2-8}$ alkenyl, halogen, phenyl, C$_{1-6}$ alkoxy, amine di-substituted with C$_{1-6}$ alkyl groups independently selected, —NHC(O)R$_3$—, —C(O)NH—R$_3$, —OC(O)R$_3$, and —C(O)OR$_3$—, wherein R$_3$ is C$_{1-6}$ alkyl,
c) a 5-6 membered aromatic ring having one or more heteroatoms selected from N, S, and O and being optionally substituted with one or more groups independently selected from:
    C$_{1-8}$ alkyl, linear or branched C$_{2-8}$ alkenyl, C$_{5-6}$ cycloalkyl phenyl as defined in b)
    5-6 membered aromatic ring group
    halogen,
    (C$_{1-6}$alkyl)OCH$_2$—, C$_{1-6}$ alkoxy,
    amino di-substituted with C$_{1-6}$ alkyl groups,
    NHC(O)R$_3$—, —C(O)NH—R$_3$, —OC(O)R$_3$, and —C(O)OR$_3$—, wherein R$_3$ is C$_{1-6}$ alkyl
d) a bicyclic ring containing at least one phenyl group and a C$_{5-6}$ aromatic heterocyclic group having one or more heteroatoms selected from N, S, and O, wherein the phenyl group of said bicyclic ring is optionally substituted with one or more groups independently selected from
    C$_{1-8}$ alkyl, linear or branched C$_{2-8}$ alkenyl, C$_{5-6}$ cycloalkyl phenyl as defined in b)
    5-6 membered aromatic ring group
    halogen,
    (C$_{1-6}$alkyl)OCH$_2$—, C$_{1-6}$alkoxy
    amino di-substituted with C$_{1-6}$ alkyl groups
    NHC(O)R$_3$—, —C(O)NH—R$_3$, —OC(O)R$_3$, and —C(O)OR$_3$—, wherein R$_3$ is C$_{1-6}$ alkyl, and
e) —CH(R$_4$)—CH(R$_5$)COOH, wherein R$_4$ is selected from H, NH$_2$, OH and CH$_2$COOH, and wherein R$_5$ is selected from H, NH$_2$, OH and CH$_2$COOH.

"Alkyl" refers to a linear or branched hydrocarbon chain radical consisting of carbon and hydrogen atoms, containing no unsaturation, and which is attached to the rest of the molecule by a single bond. In a preferred embodiment, the alkyl groups have 1, 2, 3, 4, 5, 6, 7 or 8 carbon atoms. Methyl, ethyl, n-propyl, iso-propyl and butyl, pentyl, hexyl, heptyl, including n-butyl, tert-butyl, sec-butyl and iso-butyl are particularly preferred alkyl groups. As used herein, the term alkyl, unless otherwise stated, refers to both cyclic and noncyclic groups, although cyclic groups will comprise at least three carbon ring members, such as cyclopropyl or cyclohexyl. Alkyl radicals may be optionally substituted by one or more substituents, such as an aryl group, like in benzyl or phenethyl. In a more preferred embodiment, the alkyl is C$_1$-C$_6$ alkyl. In a more preferred embodiment, the C$_1$-C$_6$ alkyl is selected from the group consisting of —CH$_3$, —CH$_2$CH$_3$, —(CH$_2$)$_2$CH$_3$, —(CH$_2$)$_3$CH$_3$, —(CH$_2$)$_4$CH$_3$ and —(CH$_2$)$_5$CH$_3$.

"Alkenyl" refers to an unsaturated branched, straight-chain, or cyclic hydrocarbon group having at least one carbon-carbon double bond derived by the removal of one hydrogen atom from a single carbon atom of a parent alkene. In the context of the present invention, the alkenyl groups have 1, 2, 3, 4, 5, 6, 7 or 8 carbon atoms. The group may be in either the Z- or E-form (cis or trans) about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl; and the like. An alkenyl group having 2 to 8 carbon atoms is referred as a —(C$_2$-C$_8$)alkenyl group.

The term "halo" or "halogen" means fluorine, chlorine, bromine or iodine.

The term "halo alkyl" refers to an alkyl group as defined above wherein at least one of the hydrogen atoms has been replaced by a halogen atom such as for example CF$_3$, CHF$_2$, CH$_2$F, CF$_2$CF$_3$ etc.

"Alkoxy" refers to a radical —OR where R represents an alkyl group as defined herein. In particular the term "C$_{1-6}$ alkoxy" refers to a radical —OR where R is an alkyl group having from 1 to 6 carbon atoms. Representative examples include, but are not limited to, methoxy, ethoxy, propoxy, butoxy, cyclohexyloxy, and the like.

"Cycloalkyl" refers to a saturated or unsaturated, but non-aromatic, cyclic alkyl group. In the context of the present invention the cycloalkyl group can be C$_{5-6}$ cycloalkyl, such as cyclopentane or cyclohexane.

The term "bicyclic ring" refers to two cyclic groups fused to form a bicyclic group, wherein one of the cyclic groups is a phenyl group and the other cyclic group is a C$_{5-6}$ aromatic heterocyclic group having one or more heteroatoms selected from N, S, and O. The phenyl group of the bicyclic ring may optionally substituted with C$_{1-8}$ alkyl, linear or branched C$_{2-8}$ alkenyl, C$_{5-6}$ cycloalkyl, phenyl optionally substituted with one or more groups independently selected from C$_{1-8}$ alkyl, C$_{2-8}$ alkenyl, halogen, phenyl, C$_{1-6}$ alkoxy, amine di-substituted with C$_{1-6}$ alkyl groups independently selected, —NHC(O)R$_3$—, —C(O)NH—R$_3$, —OC(O)R$_3$, and —C(O)OR$_3$—, wherein R$_3$ is C$_{1-6}$ alkyl, 5-6 membered aromatic ring group, halogen, (C$_{1-6}$alkyl)OCH$_2$—, C$_{1-6}$ alkoxy, amino di-substituted with C$_{1-6}$ alkyl groups, NHC(O)R$_3$—, —C(O)NH—R$_3$, —OC(O)R$_3$, and —C(O)OR$_3$—, wherein R$_3$ is C$_{1-6}$ alkyl.

"Aryl" as used herein relates to single and multiple ring compounds, including multiple ring compounds that contain separate and/or fused aryl groups. Typical aryl groups contain from 1 to 3 separated and/or fused rings and from 6 to about 18 carbon ring atoms. Preferably aryl groups contain from 6 to about 10 carbon ring atoms. Specially preferred aryl groups include substituted or unsubstituted phenyl, substituted or unsubstituted naphthyl, substituted or unsubstituted biphenyl, substituted or unsubstituted phenanthryl and substituted or unsubstituted anthryl. The term includes but is not limited to, phenyl, naphthyl, tetrahydronaphthyl, indanyl, indenyl, and the like. In a preferred embodiment the aryl is phenyl.

"Heterocyclic", "heterocyclo" or "heterocyclyl" refer to cyclic hydrocarbon group in which one or more carbon atoms (and any associated hydrogen atoms) are independently replaced with the same or a different heteroatom selected from N, O, and S. In some embodiments, a heterocyclyl group includes 3 to 10 ring members of which 1, 2, or 3 ring members are independently selected from N, O, or S. In other embodiments, a heterocyclyl group includes 5 to 7 ring members of which 1, 2, or 3 are heteroatoms independently selected from N, O, or S.

The term "optionally substituted" means unsubstituted or substituted with one or more substituents having one or more different functional groups in one or more positions. As understood in this technical area, there can be a certain degree of substitution on the previously defined radicals. The term "substituted" whether preceded by the term "optionally" or not, and substituents contained in formulas of the invention, refer to the replacement of hydrogen radicals in a given structure with the radical of a specified substituent. When more than one position in any given structure may be substituted with more than one substituent selected from a specified group, the substituent may be the same or different at every position.

In one embodiment, the compound according to the invention is the compound of formula:

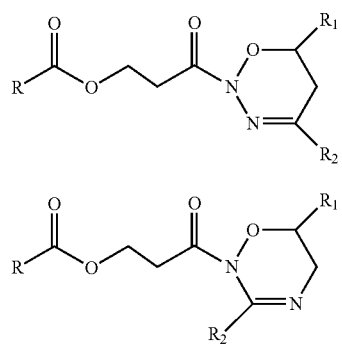

or a pharmaceutically acceptable salt, stereoisomer or solvate thereof.

In a particular embodiment, the invention refers to the compound according to the invention wherein $R_1$ and $R_2$ are the same group, or to a pharmaceutically acceptable salt, stereoisomer or solvate thereof. Preferably, $R_1$ and $R_2$ are —$(CH_2)_4$—$CH_3$. Therefore, the compound of the invention is selected from:

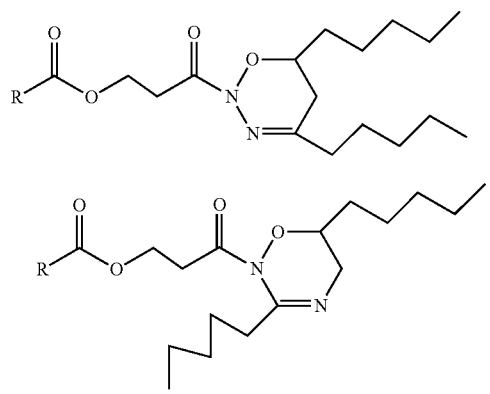

or a pharmaceutically acceptable salt, stereoisomer or solvate thereof. In a more preferred embodiment the compound of the invention is compound (IV).

In one particular embodiment the invention refers to the compound according to the invention wherein R is a methyl group or —$(CH_2)_2$—COOH, or a pharmaceutically acceptable salt, stereoisomer or solvate thereof. Therefore, the compound of the invention is selected from:

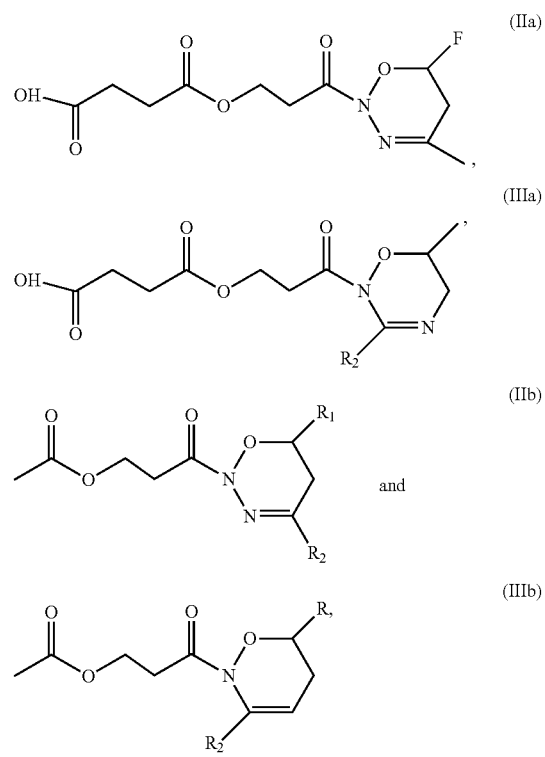

In a more preferred embodiment R is a methyl group, and $R_1$ and $R_2$ are —$(CH_2)_4$—$CH_3$. Therefore, the compound of the invention is selected from:

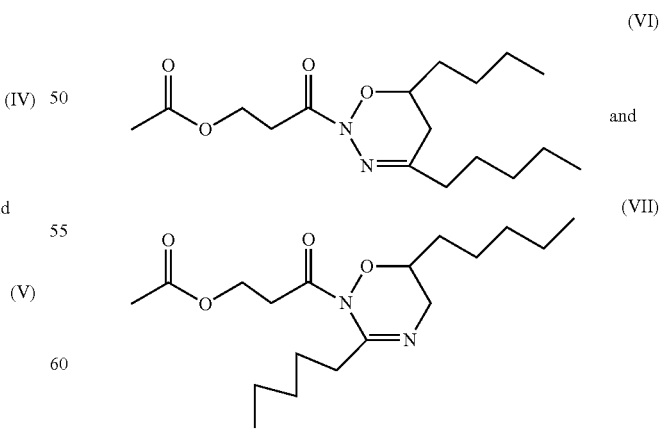

In another preferred embodiment R is —$(CH_2)_2$—COOH and $R_1$ and $R_2$ are —$(CH_2)_4$—$CH_3$. Therefore the compound of the invention is selected from:

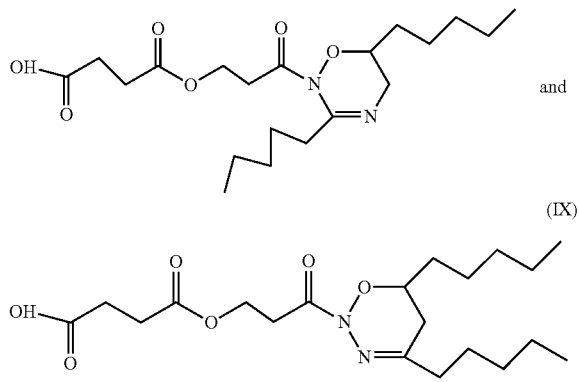

(VIII) and (IX)

Compounds IX and VI are referred in the context of the present invention as DOXA-1 and DOXA-2 respectively.

In a more preferred embodiment the compound is selected from

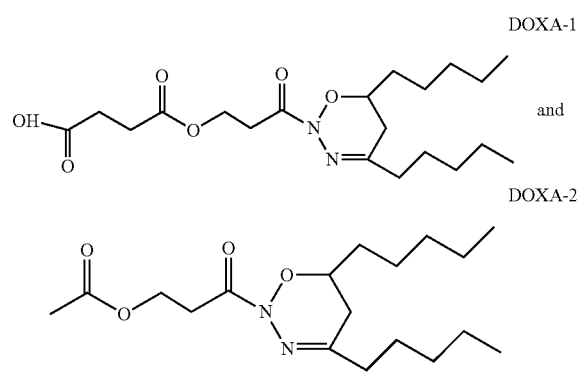

DOXA-1 and DOXA-2

The invention also relates to a pharmaceutically acceptable salt, stereoisomer or solvate of a compound of the invention.

The term "salt" is to be understood as meaning any form of the active compound according to the invention in which this assumes an ionic form or is charged and is coupled with a counter-ion (a cation or anion) or is in solution. By this are also to be understood complexes of the active compound with other molecules and ions, in particular complexes which are complexed via ionic interactions. The definition includes in particular physiologically acceptable salts; this term must be understood as equivalent to "pharmacologically acceptable salts" or "pharmaceutically acceptable salts".

The term "physiologically acceptable salt" or "pharmaceutically acceptable salt" is understood in particular, in the context of this invention, as a salt (as defined above) formed either with a physiologically tolerated acid, that is to say salts of the particular active compound with inorganic or organic acids which are physiologically tolerated—especially if used on humans and/or mammals—or with at least one, preferably inorganic, cation which are physiologically tolerated—especially if used on humans and/or mammals.

For instance, pharmaceutically acceptable salts of compounds provided herein are synthesized from the parent compound, which contains a basic or acidic moiety, by conventional chemical methods. Generally, such salts are, for example, prepared by reacting the free acid or base forms of these compounds with a stoichiometric amount of the appropriate base or acid in water or in an organic solvent or in a mixture of both. Generally, non-aqueous media like ether, ethyl acetate, ethanol, 2-propanol or acetonitrile are preferred. Examples of the acid addition salts include mineral acid addition salts such as, for example, hydrochloride, hydrobromide, hydroiodide, sulfate, nitrate, phosphate, and organic acid addition salts such as, for example, acetate, trifluoroacetate, maleate, fumarate, citrate, oxalate, succinate, tartrate, malate, mandelate, methanesulfonate and p-toluenesulfonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic aminoacids salts. Since hydroxytyrosol has three hydroxyl groups, alkali addition salts are particularly preferred such as Na+ and NX4+ (wherein X is independently selected from H or a C1-C4 alkyl group).

For those persons skilled in the art, it will be evident that the scope of the present invention also includes salts which are not pharmaceutically acceptable as possible means for obtaining pharmaceutically acceptable salts.

Any compound referred to herein is intended to represent such specific compound as well as certain variations or forms. Compounds of the present invention represented by the above described formula (I) include stereoisomers. The term "stereoisomer" as used herein includes any enantiomer, diastereomer or geometric isomer (E/Z) of such compound. In particular, compounds referred to herein may have asymmetric centres and therefore exist in different enantiomeric or diastereomeric forms. Thus any given compound referred to herein is intended to represent any one of a racemate, one or more enantiomeric forms, one or more diastereomeric forms, and mixtures thereof. Likewise, stereoisomerism or geometric isomerism related to a double bond is also possible, therefore in some cases the molecule could exist as (E)-isomer or (Z)-isomer (trans and cis isomers). If the molecule contains several double bonds, each double bond will have its own stereoisomerism, that could be the same or different than the stereoisomerism of the other double bonds of the molecule. All the stereoisomers including enantiomers, diastereoisomers and geometric isomers of the compounds referred to herein, and mixtures thereof, are considered within the scope of the present invention.

Compounds of the invention may be in crystalline form either as free compounds or as solvates (e.g. hydrates, alcoholates, particularly methanolates) and it is intended that both forms are within the scope of the present invention. Solvate may include water or non-aqueous solvents such as ethanol, isopropanol, DMSO, acetic acid, ethanolamine, and EtOAc. Solvates, wherein water is the solvent molecule incorporated into the crystal lattice, are typically referred to as "hydrates". Hydrates include stoichiometric hydrates as well as compositions containing variable amounts of water. Methods of solvation are generally known within the art.

When a disclosed compound is named or depicted by structure, it is to be understood that the compound, including solvates thereof, may exist in crystalline forms, non-crystalline forms or a mixture thereof. Compounds or solvates may also exhibit polymorphism (i.e. the capacity to occur in different crystalline forms). These different crystalline forms are typically known as "polymorphs". It is to be understood that when named or depicted by structure, the disclosed compounds and solvates (e.g., hydrates) also include all polymorphs thereof. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjusting the conditions used in solidifying the compound. For example, changes in temperature, pressure, or solvent may result in different polymorphs. In addition, one polymorph may spontaneously convert to another polymorph under certain conditions.

Furthermore, any compound referred to herein may exist as tautomers. Specifically, the term tautomer refers to one of two or more structural isomers of a compound that exist in equilibrium and are readily converted from one isomeric form to another. Common tautomeric pairs are enamine-imine, amide-imidic acid, keto-enol, lactam-lactim, etc.

Unless otherwise stated, the compounds of the invention are also meant to include isotopically-labelled forms i.e. compounds which differ only in the presence of one or more isotopically-enriched atoms. For example, compounds having the present structures except for the replacement of at least one hydrogen atom by a deuterium or tritium, or the replacement of at least one carbon by $^{13}$C- or $^{14}$C-enriched carbon, or the replacement of at least one nitrogen by $^{15}$N-enriched nitrogen are within the scope of this invention.

Compounds of formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its pharmaceutically acceptable salt, stereoisomer or solvate.

The invention also provides "metabolites" of the compounds described in the present description. A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups.

The invention also provides "prodrugs" of the compounds described in the present description. The term "prodrug", as used herein, is intended to represent covalently bonded carriers, which are capable of releasing the compound of formula (I) as active ingredient when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups by routine manipulation or in vivo. Prodrugs of compounds of the invention include compounds wherein a hydroxy, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy or amino functional groups in compounds of Formula (I)), amides (e.g., trifluoroacetylamino, acetylamino, and the like), and the like.

In additional preferred embodiments, the preferences described above for the different groups and substituents in the formulae above are combined. The present invention is also directed to such combinations.

Pharmaceutical Composition of the Invention

In a second aspect, the invention relates to a pharmaceutical composition comprising a compound of the invention or a pharmaceutically acceptable salt, stereoisomer or solvate thereof and a pharmaceutically acceptable excipient.

"Pharmaceutical composition" as used herein, relates to compositions and molecular entities that are physiologically tolerable and do not typically produce an allergic reaction or a similar unfavorable reaction as gastric disorders, dizziness and suchlike, when administered to a human or animal. Preferably, the term "pharmaceutically acceptable" means it is approved by a regulatory agency of a state or federal government and/or is included in the U.S. Pharmacopoeia and/or other generally recognized pharmacopoeia for use in animals, and more particularly in humans.

The term "excipient" refers to a vehicle, diluent or adjuvant that is administered with the active ingredient. Such pharmaceutical excipients can be sterile liquids, such as water and oils, including those of petroleum, animal, vegetable or synthetic origin, such as peanut oil, soybean oil, mineral oil, sesame oil and similars. Water or saline aqueous solutions and aqueous dextrose and glycerol solutions, particularly for injectable solutions, are preferably used as vehicles. Suitable pharmaceutical vehicles are described in "Remington's Pharmaceutical Sciences" by E. W. Martin, 21 Edition, 2005; or "Handbook of Pharmaceutical Excipients", Rowe C. R.; Paul J. S.; Marian E. Q., sixth Edition Appropriate amounts of a compound of formula (I) as defined above, or a pharmaceutically acceptable salt, stereoisomer or solvate thereof can be formulated with pharmaceutically acceptable excipients and/or carriers to obtain a pharmaceutical composition for use in medicine, particularly in preventing and/or treating an infection caused by a bacterium, fungi or virus or preventing and/or treating cancer.

Suitable pharmaceutically acceptable vehicles include, for example, water, salt solutions, alcohol, vegetable oils, polyethylene glycols, gelatin, lactose, amylose, magnesium stearate, talc, surfactants, silicic acid, viscous paraffin, perfume oil, monoglycerides and diglycerides of fatty acids, fatty acid esters petroetrals, hydroxymethyl cellulose, polyvinylpyrrolidone and similars.

The pharmaceutical compositions containing the compound of formula (I) as defined above, or a pharmaceutically acceptable salt, stereoisomer or solvate thereof according to the invention can occur at any pharmaceutical form of administration considered appropriate for the selected administration route, for example, by systemic (e.g intravenous, subcutaneous, intramuscular injection), oral, parenteral or topical administration, for which it will include the pharmaceutically acceptable excipients necessary for formulation of the desired method of administration. Additionally, it is also possible to administer the composition comprising the compound of formula (I) as defined above, or a pharmaceutically acceptable salt, stereoisomer or solvate thereof of the invention intranasally or sublingually which allows systemic administration by a non-aggressive mode of administration. Also, intraventricular administration may be adequate. A preferred route of delivery is oral.

Those skilled in the art are familiar with the principles and procedures discussed in widely known.

Where necessary, the compound of formula (I) as defined above, or a pharmaceutically acceptable salt, stereoisomer or solvate thereof is comprised in a composition also including a solubilizing agent and a local anesthetic to ameliorate any pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided so that the ingredients may be mixed prior to administration.

In cases other than intravenous administration, the composition can contain minor amounts of wetting or emulsifying agents, or pH buffering agents. The composition can be a liquid solution, suspension, emulsion, gel, polymer, or sustained release formulation. The composition can be formulated with traditional binders and carriers, as would be known in the art. Formulations can include standard carriers such as pharmaceutical grades of mannitol, lactose, starch, magnesium stearate, sodium saccharide, cellulose, magnesium carbonate, etc., inert carriers having well established functionality in the manufacture of pharmaceuticals. Various delivery systems are known and can be used to administer a therapeutic of the present invention including encapsulation in liposomes, microparticles, microcapsules and the like.

Solid dosage forms for oral administration may include conventional capsules, sustained release capsules, conventional tablets, sustained-release tablets, chewable tablets, sublingual tablets, effervescent tablets, pills, suspensions, powders, granules and gels. At these solid dosage forms, the active compounds can be mixed with at least one inert excipient such as sucrose, lactose or starch. Such dosage forms can also comprise, as in normal practice, additional substances other than inert diluents, e.g. lubricating agents such as magnesium stearate. In the case of capsules, tablets, effervescent tablets and pills, dosage forms may also comprise buffering agents. Tablets and pills can be prepared with enteric coatings.

Liquid dosage forms for oral administration may include emulsions, solutions, suspensions, syrups and elixirs pharmaceutically acceptable containing inert diluents commonly used in the technique, such as water. Those compositions may also comprise adjuvants such as wetting agents, emulsifying and suspending agents, and sweetening agents, flavoring and perfuming agents.

Injectable preparations, for example, aqueous or oleaginous suspensions, sterile injectable may be formulated according with the technique known using suitable dispersing agents, wetting agents and/or suspending agents. Among the acceptable vehicles and solvents that can be used are water, Ringer's solution and isotonic sodium chloride solution. Sterile oils are also conventionally used as solvents or suspending media.

For topical administration, the compounds of the invention can be formulated as creams, gels, lotions, liquids, pomades, spray solutions, dispersions, solid bars, emulsions, microemulsions and similars which may be formulated according to conventional methods that use suitable excipients, such as, for example, emulsifiers, surfactants, thickening agents, coloring agents and combinations of two or more thereof.

Additionally, the compounds of formula (I) as defined above, or a pharmaceutically acceptable salt, stereoisomer or solvate thereof may be administered in the form of transdermal patches or iontophoresis devices. In one embodiment, the compounds of the invention are administered as a transdermal patch, for example, in the form of sustained-release transdermal patch. Suitable transdermal patches are known in the art.

Several drug delivery systems are known and can be used to administer the agents or compositions of the invention, including, for example, encapsulation in liposomes, microbubbles, emulsions, microparticles, microcapsules and similars. The required dosage can be administered as a single unit or in a sustained release form.

Sustainable-release forms and appropriate materials and methods for their preparation are described in, for example, "Modified-Release Drug Delivery Technology", Rathbone, M. J. Hadgraft, J. and Roberts, M. S. (eds.), Marcel Dekker, Inc., New York (2002), "Handbook of Pharmaceutical Controlled Release Technology", Wise, D. L. (ed.), Marcel Dekker, Inc. New York, (2000). In one embodiment of the invention, the orally administrable form of a compound according to the invention is in a sustained release form further comprises at least one coating or matrix. The coating or sustained release matrix include, without limitation, natural polymers, semisynthetic or synthetic water-insoluble, modified, waxes, fats, fatty alcohols, fatty acids, natural semisynthetic or synthetic plasticizers, or a combination of two or more of the them. Enteric coatings may be applied using conventional processes known to experts in the art, as described in, for example, Johnson, J. L., "Pharmaceutical tablet coating", Coatings Technology Handbook (Second Edition), Satas, D. and Tracton, A. A. (eds), Marcel Dekker, Inc. New York, (2001), Carstensen, T., "Coating Tablets in Advanced Pharmaceutical Solids", Swarbrick, J. (ed.), Marcel Dekker, Inc. New York (2001), 455-468.

The present invention also encompasses the combination of the compounds of formula (I) or of its pharmaceutically acceptable salt, stereoisomer or solvate with other antimicrobial drugs or cancer chemotherapeutic agents. A combination of at least a compound of formula (I) and at least another antimicrobial drug or cancer chemotherapeutic agents may be formulated for its simultaneous, separate or sequential administration. This has the implication that the combination of the two compounds may be administered:

as a combination that is being part of the same medicament formulation, the two compounds being then administered always simultaneously.

as a combination of two units, each with one of the substances giving rise to the possibility of simultaneous, sequential or separate administration.

In a particular embodiment, the compound of formula (I) is independently administered from the other antimicrobial drug or cancer chemotherapeutic agent (i.e in two units) but at the same time.

In another particular embodiment, the compound of formula (I) is administered first, and then the other antimicrobial drug or cancer chemotherapeutic agent is separately or sequentially administered.

In yet another particular embodiment, the other antimicrobial drug or cancer chemotherapeutic agent is administered first, and then the compound of formula (I) is administered, separately or sequentially, as defined.

"Antimicrobial drug", as used herein, relates to any drug capable of killing bacteria, viruses, fungi or parasites or inhibit their growth. Antimicrobial medicines can be grouped according to the microorganisms they act primarily against, antibacterial, antifungal, antiviral and antiparasitic.

The term "cancer chemotherapeutic agent" includes standard chemotherapy drugs, which generally attack any quickly dividing cell, targeted therapy agents and immunomodulatory agents.

Illustrative non-limitative examples of cancer chemotherapeutic agents which may be in accordance to the present invention include alkylating agents, antimetabolite drugs, anthracycline antibiotics, antibodies targeted against proangiogenic factors, topoisomerase inhibitors, antimicrotubule agents, low molecular weight tyrosine kinases inhibitors of proangiogenic growth factors and matrix metalloproteinase inhibitors.

In additional preferred embodiments, the preferences described above for the different groups and substituents in the formulae above are combined. The present invention is also directed to such combinations.

Process for Obtaining the Compounds of the Invention

In a third aspect, the invention relates to a method for preparing a compound of formula (I) or a pharmaceutically acceptable salt, stereoisomer or solvate thereof, according to claim 1 comprising reacting a compound of formula (X) in the presence of triethylamine and a solvent:

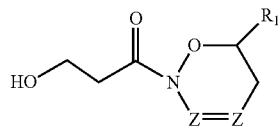

(X)

wherein one Z is N and the other is —C—$R_2$; and $R_2$ and $R_1$ are independently selected from the group consisting of H, alkyl and aryl,
with a compound of formula (XI)

(XI)

wherein X is selected from an halogen and —(O)C(O)R, wherein R is selected from a group consisting of
a) a linear or branched $C_{1-8}$ alkyl, a linear or branched $C_{2-8}$ alkenyl, di-halo methyl, tri-halo methyl, $C_{5-6}$ cycloalkyl, ($C_{1-6}$ alkyl)OCH$_2$—, amine di-substituted with $C_{1-6}$ alkyl groups independently selected,
b) phenyl optionally substituted with one or more groups independently selected from $C_{1-8}$ alkyl, $C_{2-8}$ alkenyl, halogen, phenyl, $C_{1-6}$ alkoxy, amine di-substituted with $C_{1-6}$ alkyl groups independently selected, —NHC(O)$R_3$—, —C(O)NH—$R_3$, —OC(O)$R_3$, and —C(O)O$R_3$—, wherein $R_3$ is $C_{1-6}$ alkyl,
c) 5-6 membered aromatic ring having one or more heteroatoms selected from N, S, and O and being optionally substituted with one or more groups independently selected from:

$C_{1-8}$ alkyl, linear or branched $C_{2-8}$ alkenyl, $C_{5-6}$ cycloalkyl phenyl as defined in b)
5-6 membered aromatic ring group
halogen,
($C_{1-6}$alkyl)OCH$_2$—, $C_{1-6}$ alkoxy,
amino di-substituted with $C_{1-6}$ alkyl groups,
NHC(O)$R_3$—, —C(O)NH—$R_3$, —OC(O)$R_3$, and —C(O)OR$_3$—, wherein $R_3$ is $C_{1-6}$ alkyl
d) bicyclic ring containing at least one phenyl group and a $C_{5-6}$ aromatic heterocyclic group having one or more heteroatoms selected from N, S, and O, wherein the phenyl group of said bicyclic ring is optionally substituted with one or more groups independently selected from
$C_{1-8}$ alkyl, linear or branched $C_{2-8}$ alkenyl, $C_{5-6}$ cycloalkyl phenyl as defined in b)
5-6 membered aromatic ring group
halogen,
($C_{1-6}$alkyl)OCH$_2$—, $C_{1-6}$ alkoxy
amino di-substituted with $C_{1-6}$ alkyl groups
NHC(O)$R_3$—, —C(O)NH—$R_3$, —OC(O)$R_3$, and —C(O)OR$_3$—, wherein $R_3$ is $C_{1-6}$ alkyl, and
e) —CH($R_4$)—CH($R_5$) COOH, wherein $R_3$ is selected from H, NH$_2$, OH and CH$_2$COOH, and wherein $R_5$ is selected from H, NH$_2$, OH and CH$_2$COOH,
or
reacting the compound of formula (X) with a compound of formula (XII)

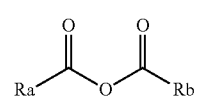

(XII)

wherein Ra and Rb together form, with the anhydride group C(O)OC(O) to which they are attached, a substituted or unsubstituted, cyclic group. Preferably, the cyclic group is a cyclopentyl group or a cyclohexyl group.

The solvent in the process of the invention may be any suitable organic solvent. In a preferred embodiment, the organic solvent is selected from dichloromethane, THF, DMF or acetonitrile, more preferably the organic solvent is dichloromethane.

In a particular embodiment a compound of formula (Xa):

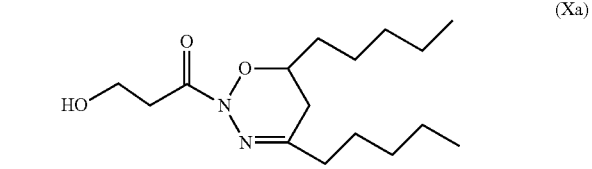 [SMILES: CCCCCC1=NN(C(=O)CCO)OC(CCCCC)C1]

(Xa)

reacts with a compound of formula

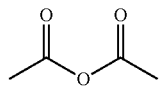

(XIa)

in the presence of triethylamine to give a compound of formula:

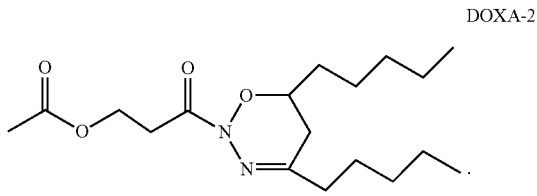 [SMILES: CCCCCC1=NN(C(=O)CCOC(C)=O)OC(CCCCC)C1]

DOXA-2

In another particular embodiment a compound of formula (Xa) as above disclosed reacts with a compound of formula (XIIa):

(XIIa)

in the presence of triethylamine to give a compound of formula:

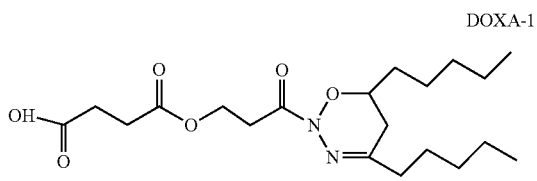 [SMILES: CCCCCC1=NN(C(=O)CCOC(=O)CCC(=O)O)OC(CCCCC)C1]

DOXA-1

Medical Uses

In a fourth aspect, the invention relates to a compound of the invention or a pharmaceutical composition of the invention for use in medicine.

In a fifth aspect, the invention relates to a compound of the invention or a pharmaceutical composition of the invention for use in preventing and/or treating an infection caused by a bacterium, fungus or virus or for use in preventing and/or treating cancer.

Alternatively, the invention relates to a method for preventing and/or treating an infection caused by a bacterium, fungus or virus and/or for preventing and/or treating cancer comprising administering a compound or a pharmaceutical composition according to the invention to a subject in need thereof.

Alternatively, the invention relates to a compound or a pharmaceutical composition according to the invention for the preparation of a medicament for preventing and/or treating an infection caused by a bacterium, fungus or virus and/or for use in preventing and/or treating cancer.

As used herein, the terms "treat", "treating" and "treatment" include in general the eradication, removal, reversion, alleviation, modification, or control of the infection or cancer after its onset.

As used herein, the terms "prevention", "preventing", "preventive", "prevent" and "prophylaxis" refer to the capacity of a given substance, composition or medicament to avoid, minimize or difficult the onset or development of an infection or cancer before its onset.

The term "subject" as used herein, relates to any subject, particularly a mammalian subject, for whom therapy is desired. Mammalian subjects include humans, domestic animals, farm animals, and zoo, sports, or pet animals such as dogs, cats, guinea pigs, rabbits, rats, mice, horses, cattle, cows, and so on. In a preferred embodiment of the invention, the subject is a mammal. In a more preferred embodiment of the invention, the subject is a human.

In a preferred embodiment, the compound for use in the medical uses or method of preventing and treating according to the invention is the compound IX, referred as DOXA-1. In another preferred embodiment, the compound for use in the medical uses or method of preventing and treating according to the invention is the compound VI, referred as DOXA-2.

The term "infection", as used herein, relates to invasion by bacteria, viruses, fungi, protozoa or other microorganisms, referring to the undesired proliferation or presence of invasion of pathogenic microbes in a host organism. It includes the excessive growth of microbes that are normally present in or on the body of a mammal or other organism. More generally, a microbial infection can be any situation in which the presence of a microbial population(s) is damaging to a host mammal. Thus, a microbial infection exists when excessive numbers of a microbial population are present in or on a mammal's body, or when the effects of the presence of a microbial population(s) is damaging the cells or other tissue of a mammal.

In a preferred embodiment, the infection is caused by a bacterium.

The term "bacterium" refers to both gram-negative and gram-positive bacterial cells capable of infecting and causing disease in a mammalian host, as well as producing infection-related symptoms in the infected host, such as fever or other signs of inflammation, intestinal symptoms, respiratory symptoms, dehydration, and the like.

In one embodiment the bacteria are gram-negative bacteria. In another embodiment the bacteria are gram-positive bacteria. In another further embodiment the bacteria are gram-positive bacteria together with gram-negative bacteria. In another embodiment there is only one bacteria specie or different bacteria species; one bacteria genus or different bacteria genus, infecting or causing disease.

In some embodiments, and without limitation, the bacteria is of a genus selected from the group consisting of *Acinetobacter, Actinobacillus, Aeromonas, Aggregatibacter, Agrobacterium, Bacillus, Bordetella, Brucella, Burkholderia, Campylobacter, Chromobacterium, Cyanobacteria, Enterobacter, Erwinia, Escherichia, Francisella, Fusobacterium, Haemophihus, Helicobacter, Klebsiella, Lactobacillus, Legionella, Listeria, Micrococcus, Moraxella, Mycobacterium, Neisseria, Nitrosomas, Nocardia, Obesumhacterium, Pantoea, Pasteurella, Pediococcus, Porphyromonas, Prevotella, Proteus, Pseudomonas, Ralstonia, Rhizobium, Rhodobacter, Salmonella, Serratia, Shigella, Staphylococcus, Streptococcus, Tannerella, Treponema, Tsukamurella, Vibrio, Xenorhabdus, Yersinia* and mixtures thereof. For example, in some embodiments and without limitation, the bacteria is of a species selected from the group consisting of *Aeromonas hydrophila, Aeromonas salmonicida, Acinetobacter baumannii, Aggregatibacter actinomycetemcomitans, Agrobacterium tumefaciens, Bacillus cereus, Bacillus subtilis, Burkholderia cepacia, Campylobacter jejuni, Chromobacterium violaceum, Enterobacter agglomeran, Erwinia carotovora, Erwinia chrysanthemi, Escherichia coli, Fusobacterium nucleatum, Haemophilus influenzae, Helicobacter pylori, Lactobacillus plantarum, Listeria monocytogenes, Klebsiella pneumoniae, Micrococcus luteus, Mycobacterium tuberculosis, Neisseria meningitidis, Neisseria gonorrhoeae, Nitrosomas europaea, Nocardia carnea, Obesumbacterium proteus, Pantoea stewartii, Pediococcus acidilactici, Prevotella intermedia, Porphyromonas gingi-*

*valis, Pseudomonas aureofaciens, Pseudomonas aeruginosa, Pseudomonas phosphoreum, Pseudomonas syringae, Ralstonia solanacearum, Rhiszobium etli, Rhizobium leguminosarum, Rhodobacter sphaeroides, Salmonella typhimurium, Serratia liguefaciens, Serratia marcescens, Staphylococcus aureus, Staphylococcus epidermidis, Staphylococcus enteritis, Tannerella forsythensis, Treponema denticola, Tsukamurella pulmonis, Vihrio anguillarum, Vibrio fischeri, Vibrio cholerae, Vibrio harveyi, Vibrio parahaemolyticus, Vibrio alginolylicus, Vibrio vulnificus, Xenorhabdus nematophilus, Yersinia enterocolilica, Yersinia pestis, Yersinia pseudotuberculosis, Yersinia medievalis, Yersinia ruckeri* and mixtures thereof.

In a preferred embodiment of the medical use of a compound of formula (I) as defined above, or a pharmaceutically acceptable salt, stereoisomer or solvate thereof, the infection is caused by a Gram positive bacterium.

In another preferred embodiment, the Gram positive bacterium is from phylum Actinobacteria or from phylum Firmicutes.

In a more preferred embodiment, the bacterium from phylum Actinobacteria is a bacterium from genus *Nocardia, Tsukamurella* or *Mycobacterium* and the bacterium from phylum Firmicutes is a bacterium from genus *Staphylococcus, Bacillus* or *Enterococcus*. In a more preferred embodiment, the bacterium from the genus *Nocardia* is *N. carnea* or *N. cyriacigeorgica*, the bacterium from genus *Tsukamurella* is *T. pulmonis*, the bacterium from genus *Mycobacterium* is *M. chelonae, M. abscessus* or *M. fortuitum*, the bacterium from genus *Staphylococcus* is *S. aureus* or *S. epidermidis*, the bacterium from genus *Bacillus* is *B. cereus* and the bacterium from genus *Enterococcus* is *E. faecium* or *E. faecalis*.

In another preferred embodiment, the Gram negative bacterium is from phylum proteobacteria. In a more preferred embodiment, bacterium from phylum proteobacteria is from genus *Acinetobacter*, preferably *A. baumannii*, from genus *Pseudomonas*, preferably *P. aeruginosa* or from genus *Escherichia* preferably *E. coli*.

In another preferred embodiment of the medical use of a compound of formula (I) as defined above, or a pharmaceutically acceptable salt, stereoisomer or solvate thereof, the infection is caused by a fungus. In a more preferred embodiment, the fungus is selected from genus *Candida, Aspergillus* or *Scedosporium*. In an even more preferably embodiment, the fungus from genus *Candida* is *C. albicans, C. glabrata, C. tropicalis, C. lusitaniae, C. guilliermondi* or *C. parapsilopsis*, the fungus from genus *Aspergillus* is *A. fumigatus, A. flavus, A. niger* or *A. terreus* and the fungus from genus *Scedosporium* is *S. prolificans*.

In another preferred embodiment of the medical use of a compound of formula (I) as defined above, or a pharmaceutically acceptable salt, stereoisomer or solvate thereof, the infection is caused by a virus.

The term "virus", refers to a small infectious agent that replicates only inside the living cells of other organism.

In some embodiments, and without limitation, the virus is selected from the group consisting of adenovirus, coxsackievirus, Epstein-Bar, Hepatitis A, B or C, herpes simplex type 1, herpes simplex type 2, cytomegalovirus, herpesvirus type 8, HIV, Influenza, Measles, mumps, human papillomavirus, parainfluenza, poliovirus, rabies, respiratory syncytial, rubella, varicella-zoster. In a preferred embodiment the virus is selected from HIV, herpes simplex I, herpes simplex II, Suid herpesvirus 1 or Equine herpesvirus 1.

In another preferred embodiment, the compound of the invention or the pharmaceutical composition is for use in the prevention and/or treatment of cancer.

The term "cancer" as used herein, refers to a disease characterized by uncontrolled cell division (or by an increase of survival or apoptosis resistance) and by the ability of said cells to invade other neighbouring tissues (invasion) and spread to other areas of the body where the cells are not normally located (metastasis) through the lymphatic and blood vessels, circulate through the bloodstream, and then invade normal tissues elsewhere in the body. Depending on whether or not they can spread by invasion and metastasis, tumours are classified as being either benign or malignant: benign tumours are tumours that cannot spread by invasion or metastasis, i.e., they only grow locally; whereas malignant tumours are tumours that are capable of spreading by invasion and metastasis. As used herein, the term cancer includes, but is not limited to, the following types of cancer: breast cancer; biliary tract cancer; bladder cancer; brain cancer including glioblastomas, in particular glioblastoma multiforme, and medulloblastomas; cervical cancer; head and neck carcinoma; choriocarcinoma; colon cancer, colorectal cancer; endometrial cancer; esophageal cancer; gastric cancer; hematological neoplasms including acute lymphocytic and myelogenous leukemia; T-cell acute lymphoblastic leukemia/lymphoma; hairy cell leukemia; chronic myelogenous leukemia, multiple myeloma; AIDS-associated leukemias and adult T-cell leukemia/lymphoma; intraepithelial neoplasms including Bowen's disease and Paget's disease; liver cancer, hepatoma; lung cancer, pleural mesothelioma; lymphomas including Hodgkin's disease and lymphocytic lymphomas; neuroblastomas; oral cancer including squamous cell carcinoma; parotid gland cancer; ovarian cancer including those arising from epithelial cells, stromal cells, germ cells and mesenchymal cells; pancreatic cancer; prostate cancer; kidney cancer, suprarenal cancer; rectal cancer; sarcomas including leiomyosarcoma, rhabdomyosarcoma, liposarcoma, fibrosarcoma, and osteosarcoma; skin cancer including melanoma, Merkel cell carcinoma, Kaposi's sarcoma, basal cell carcinoma, and squamous cell cancer; cervix cancer, endometrial cancer, testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor. Other cancers will-be known to one of ordinary skill.

In a preferred embodiment, the cancer is selected from the group consisting of breast, head and neck, colon, prostate, lung, cervix, pancreatic cancer, glioblastoma and osteosarcoma. In a more preferred embodiment, the cancer is selected from the group consisting of breast, head and neck and colon.

The present invention covers any combination of compounds and diseases.

For use in the prevention and/or treatment according to the invention, the compound of formula (I) or a pharmaceutically acceptable salt, solvate or isomer thereof or the pharmaceutical composition of the invention is present in an effective amount.

The term "effective" amount or a "therapeutically effective amount" of a drug or pharmacologically active agent is meant a nontoxic but sufficient amount of the drug or agent to provide the desired effect. In the combination therapy of the present invention, an "effective amount" of one component of the combination is the amount of that compound that is effective to provide the desired effect when used in combination with the other components of the combination.

Even though individual needs vary, determination of optimal ranges for effective amounts of the agent of the invention belongs to the common experience of those experts in the art. In general, the dosage needed to provide an effective amount of such compound, which can be adjusted by one expert in the art will vary depending on age, health, fitness, sex, diet, weight, frequency of treatment and the nature and extent of impairment or illness, medical condition of the patient, route of administration, pharmacological considerations such as activity, efficacy, pharmacokinetic and toxicology profile of the particular compound used, if using a system drug delivery, and if the compound is administered as part of a combination of drugs.

The effective quantity of the compound of the invention can vary within a wide range and, in general, will vary depending on the particular circumstances of application, duration of the exposure and other considerations. In a particular embodiment, the dose ranges between 0.05 mg/kg and 50 mg/kg, more preferably between 1 mg/kg and 20 mg/kg.

In a preferred embodiment the effective amount is between about between about 0.005% and about 0.04% weight, between about 0.0075% weight and about 0.0375% weight, between about 0.001% weight and about 0.035% weight, between about 0.00125% weight and about 0.0325% weight, between about 0.0015% weight and about 0.0325% weight, between about 0.00175% weight and about 0.03% weight, and more preferably between about 0.0018% weight and about 0.032% weight. In a particular embodiment, the effective amount is between about 0.005% and about 0.02% weight, preferably between about 0.005% weight and about 0.015% weight, more preferably between about 0.005% weight and about 0.01% weight. In some embodiments the effective amount is about 0.001% weight, about 0.002% weight, about 0.003% weight or about 0.004% weight. The percentages (% w/w) are expressed as weight of the compound of formula (I) or a pharmaceutically acceptable salt, solvate or isomer thereof by the total weight of the composition comprising the compound or by weight of the foodstuff, foodstuff package, medical device or surface.

In another embodiment the effective amount is expressed in µg/mL or µg/g (µg of the compound of formula (I) or a pharmaceutically acceptable salt, solvate or isomer thereof by mL or g of the composition comprising the compound), therefore effective amount is about 75 and about 375 µg/mL (or g/g), between about 100 and about 350 µg/mL (or µg/g), between about 125 and about 325 µg/mL (or µg/g), between about 150 and about 325 µg/mL (or g/g), between about 175 and about 300 µg/mL (or µg/g), and more preferably between about 180 and about 320 µg/mL (or µg/g). In a particular embodiment, the effective amount is between about 50 and about 200 µg/mL (or µg/g), preferably between 50 and about 150 µg/mL (or µg/g), more preferably between about 50 and about 100 µg/mL (or µg/g). In some embodiments the effective amount is about 100 µg/mL (or µg/g), about 200 µg/mL (or µg/g), about 300 µg/mL (or g/g) or about 400 g/mL (or µg/g).

When the compound of formula (I) or a salt, solvate or isomer thereof as defined herein is present on a surface, it is preferably in an effective amount of between about 1 and about 200 µg/cm², preferably between about 1 and about 100 µg/cm², preferably between about 1 and about 50 µg/cm², more preferably between about 5 and about 300 µg/cm².

The invention will be described by way of the following examples which are to be considered as merely illustrative and not limitative of the scope of the invention.

Materials and Methods

Production of the Compounds

Synthesis of DOXA-1

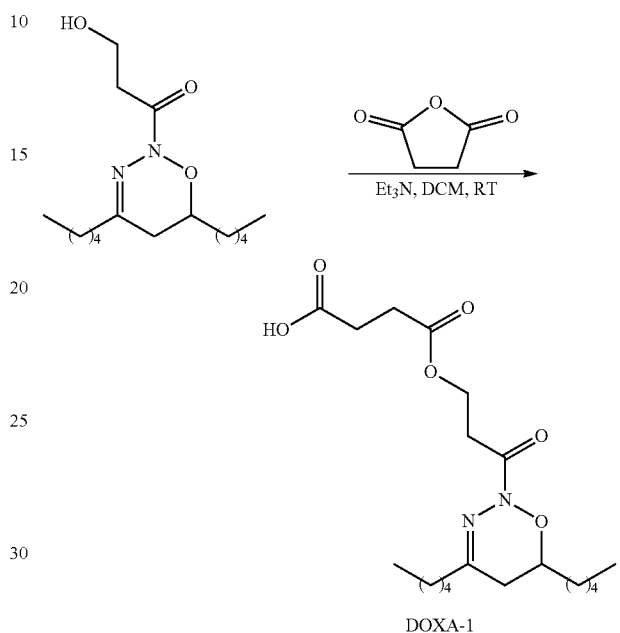

DOXA-1

Triethylamine (7 µl, 0.048 mmol, 1.1 eq.), followed by succinic anhydride (5 mg, 0.048 mmol, 1.1 eq.) were added to a solution of 1-(4,6-dipentyl-5,6-dihydro-2H-1,2,3-oxadiazin-2-yl)-3-hydroxypropan-1-one (13 mg, 0.044 mmol, 1.0 eq.) in DCM (2 ml). The mixture was stirred at room temperature for 5 h, and then concentrated under reduced pressure. The oily residue was applied to silica chromatography eluting with Heptanes/EtOAc (1:2) to gives DOXA.1 as a yellow oil. $^{1}$H-NMR (300 MHz, CDCl$_3$): δ 0.89 (m, 6H), 1.2-1.35 (m, 11H), 1.44-1.61 (m, 4H), 1.70 (m, 1H), 2.16 (dd, J=18.1, 8.9 Hz, 1H), 2.25 (t, J=6.9 Hz, 2H), 2.27 (dd, J=18.1, 3.9 Hz, 1H), 2.63 (m, 3H), 2.94 (m, 2H), 4.01 (m, 1H), 4.43 (t, J=6.4 Hz, 2H). $^{13}$C-NMR (75 MHz, CDCl$_3$): δ 14.1 (2 CH$_3$), 22.5 (CH$_2$), 22.6 (CH$_2$), 24.4 (CH$_2$), 25.8 (CH$_2$), 29.0 (CH$_2$), 29.1 (CH$_2$), 31.5 (CH$_2$), 31.8 (2 CH$_2$), 33.3 (CH$_2$), 34.0 (CH$_2$), 37.2 (CH$_2$), 60.5 (CH$_2$), 75.5 (CH), 165.0 (C), 172.1 (C), 176.4 (C).

Amount obtained: 9 mg, 60% yield.

Synthesis of DOXA-2

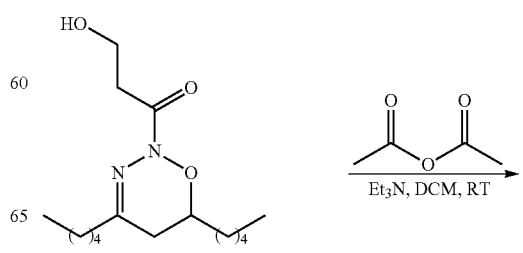

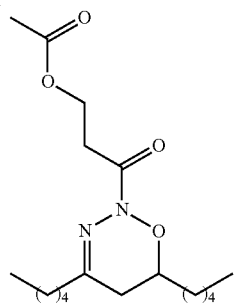

DOXA-2

Triethylamine (4 μl, 0.03 mmol, 1 eq.), followed by acetic anhydride (3 μl, 0.036 mmol, 1.1 eq.) were added to a solution of 1-(4,6-dipentyl-5,6-dihydro-2H-1,2,3-oxadiazin-2-yl)-3-hydroxypropan-1-one (10 mg, 0.03 mmol, 1.0 eq.) in DCM (2 ml). The mixture was stirred at room temperature for 2 h, and then concentrated under reduced pressure. The oily residue was applied to silica chromatography eluting with Heptanes/EtOAc (2:1) to gives DOXA.2 as a yellow oil. 1H-NMR (300 MHz, CDCl$_3$): δ 0.89 (m, 6H), 1.30-1.35 (m, 8H), 1.44-1.61 (m, 5H), 1.70 (m, 1H), 2 (s, 3H), 2.16 (dd, J=18.1, 8.9 Hz, 1H), 2.23 (t, J=6.9 Hz, 2H), 2.27 (dd, J=18.1, 3.9 Hz, 1H), 2.94 (m, 2H), 4.01 (m, 1H), 4.43 (t, J=6.4 Hz, 2H). 13C-NMR (75 MHz, CDCl3): δ 14.1 (2 CH$_3$), 21.1 (CH$_3$), 22.5 (CH$_2$), 22.6 (CH$_2$), 24.4 (CH$_2$), 25.8 (CH$_2$), 31.5 (CH$_2$), 31.8 (2 CH$_2$), 33.3 (CH$_2$), 34.1 (CH$_2$), 37.2 (CH$_2$), 60.2 (CH$_2$), 75.4 (CH), 165.0 (C), 171.1 (C).

Amount obtained: 9 mg, 88% yield.

Example 1—Antibacterial Activity

Bacterial Strains and Inoculum Preparation

Bacterial strains, from clinical origin, were supplied by the National Center for Microbiology, Institute of Health Carlos III (Majadahonda, Madrid). They are detailed in Table I.

| Specie | Strain | Isolation year | IMP | CTX | A/C | LIN | AMK | SxT | CIP |
|---|---|---|---|---|---|---|---|---|---|
| N. cyriacigeorgica | 30 | 2005 | S | S | R | S | S | S | R |
| N cyriacigeorgica | 199 | 2005 | R | R | R | S | R | S | R |
| N. carnea | 769 | 2009 | S | S | S | S | S | R | S |
| N. carnea | 40 | 2011 | R | S | S | S | R | R | S |
| T. pulmonis | 1991 | 2009 | S | S | S | S | S | S | S |
| T. pulmonis | 40 | 2015 | S | R | R | R | R | R | R |
| M. chelonae | 870 | 2011 | R | | | R | | R | R |
| M. abscessus | 690 | 2012 | R | | | S | | S | R |
| M. fortuitum | 1080 | 2011 | R | | | R | | S | S |
| B. cereus | 25 | 2014 | | | | | | | |
| B. cereus | 182 | 2013 | | | | | | | |
| A. baumannii | 300 | 2001 | R | | | | R | | R |
| A. baumannii | 1301 | 2009 | S | | | | S | | S |
| S. aureus | 282 | 2005 | | | | | S | | R |
| S. aureus | 890 | 2010 | | | | | S | | S |
| S. epidermidis | 982 | 2006 | | | | | S | | R |
| S. epidermidis | 188 | 2009 | | | | | S | | S |
| E. faecium | 209 | 2015 | | R | | | R | | |
| E. faecium | 26 | 2012 | | R | | | S | | |
| E. faecalis | 1052 | 2008 | | R | | | S | | |
| E. faecalis | 52 | 2006 | | R | | | S | | |
| P. aeruginosa | 96 | 2014 | | S | | S | S | | |
| P. aeruginosa | 115 | 2013 | | S | | | S | | S |
| E. coli | 29 | 2012 | S | S | S | | S | | |
| E. coli | 305 | 2008 | S | R | R | | S | | |

| Specie | ERI | PEN | VAN | RIF | TET | CLI | MER | CEF | TOB | GEN |
|---|---|---|---|---|---|---|---|---|---|---|
| N. cyriacigeorgica | R | | | | | | | | | |
| N cyriacigeorgica | R | | | | | | | | | |
| N. carnea | R | | | | | | | | | |
| N. carnea | R | | | | | | | | | |
| T. pulmonis | S | | | | | | | | | |
| T. pulmonis | R | | | | | | | | | |
| M. chelonae | R | R | | | | | | | | |
| M. abscessus | S | R | | | | | | | | |
| M. fortuitum | R | R | | | | | | | | |
| B. cereus | R | S | S | S | R | R | | | | |
| B. cereus | R | S | S | S | S | R | | | | |
| A. baumannii | | | | | | | R | R | S | |
| A. baumannii | | | | | | | S | R | S | |
| S. aureus | R | | S | | S | R | | | | R |
| S. aureus | R | | S | | R | R | | | | R |
| S. epidermidis | R | | S | | S | R | | | | R |
| S. epidermidis | S | | S | | S | S | | | | S |
| E. faecium | | R | S | | | | | | | S |
| E. faecium | | R | I | | | | | | | S |
| E. faecalis | | R | S | | | | | | | S |
| E. faecalis | | R | S | | | | | | | S |
| P. aeruginosa | | | | | | | R | R | S | |
| P. aeruginosa | | | | | | | | | | |

| | | | | |
|---|---|---|---|---|
| E. coli | S | R | | S |
| E. coli | S | R | | S |

IMP = Imipenem; CTX = Cefotaxime; A/C = Amoxicillin/Clavulanate; Lin = Linezolid; AMK = Amikacin; SxT = Cotrimoxazole; CIP = Ciprofloxacin; ERI = Erythromycin; PEN = Penicillin; VAN = Vancomycin; RIF = Rifampicin; TET = Tetracycline; CLI = Clindamycin; MER = Meropenem; CEF = Ceftriazone; TOB = Tobramycin; GEN = Gentamicin.

Antibacterial Susceptibility Test

Bacterial cells suspension in sterile saline was prepared from a culture of 24-72 h, depending on bacterial species, in Mueller-Hinton Agar with 5% sheep blood. Each suspension was adjusted to a fixed size inoculum of $1-5\times10^8$ CFU/ml with a spectrophotometer (Ferraro, M J National Committee for Clinical Laboratory Standards. 2000).

Kirby-Bauer disk diffusion susceptibility test protocol was utilized to determine the sensitivity or resistance of pathogenic bacteria against the compounds and others antibiotics. The absence of growth around the disks is an indirect measure of the ability of this compound to inhibit an organism (Kirby, W. et al., Antibiotics Annu. 1956-1957: 892). After 18 to 72 hours of incubation at 370° C., with or without $CO_2$, under aerobic or anaerobic conditions, depending on the bacterial species, halo of growth inhibition were obtained and evaluated.

Antibiotic Activity

Interpretation of susceptibility and resistance was based on the presence or absence of a zone of inhibition surrounding the disk. Kirby-Bauer disk diffusion susceptibility test is a common method which uses antibiotic-impregnated wafers to test whether bacteria are affected by antibiotics. The size of the zone of inhibition depends on how effective the antibiotic is at stopping the growth of the bacterium. A stronger antibiotic will create a larger zone, because a lower concentration of the antibiotic is enough to stop growth.

Figure 2:
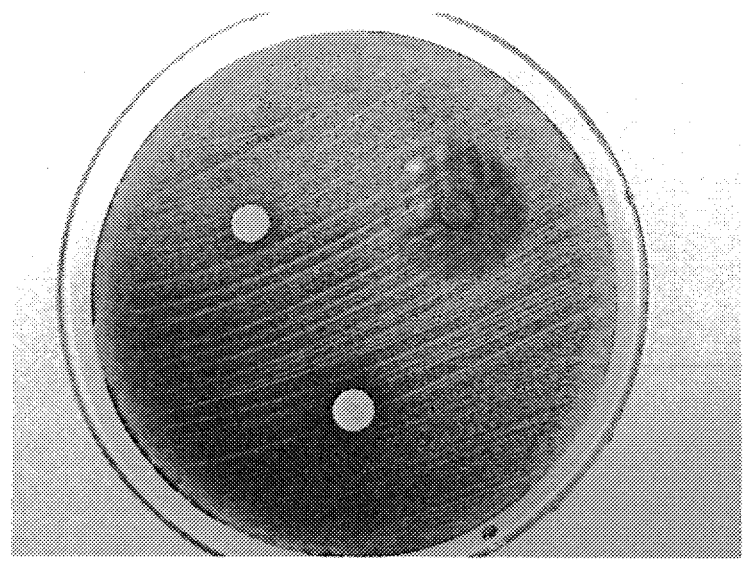
FIG. 2. Activity of the compound doxa 2 in *Mycobacterium abscessus*.

The results of antibiotic activity obtained with the Kirby-Bauer antibiotic test show the great potential of compounds, not only as molecules with specific activity against specific bacteria but also as possible structures for the development of broad spectrum antibiotics. The activity results are shown in Table II and some examples in FIGS. 1 and 2.

TABLE II

Antibiotic activities detected with the compounds.

| | Activity (mm), 200 µg/disc | |
|---|---|---|
| Species | DOXA-1 | DOXA-2 |
| N. carnea | 40 | 25 |
| N. cyriacigeorgica | 35 | 26 |
| T. pulmonis | 34 | 41 |
| M. chelonae | 34 | 30 |
| M. abscessus | 32 | 25 |
| M. fortuitum | 30 | 25 |
| S. epidermidis | 22 | 10 |
| S. aureus | 20 | 10 |
| E. faecium | 34 | — |
| E. faecalis | 34 | — |
| B. cereus | 36 | 20 |
| A. baumannii | — | 9 |
| P. aeruginosa | 9 | 9 |
| E. coli | 9 | 9 |

All compounds were tested at 200 µg/disc. The best activity was detected in *Nocardia* spp., *Tsukamurella pulmonis*, *Mycobacterium* spp., *Enterococcus* spp. with both compounds. Besides, in *Enterococcus* spp. and *Bacillus cereus* only with the compound doxa 2. Noteworthy that the activity of compound is bactericidal in all species tested, except bacteriostatic in *B. cereus*.

Example 2—Antifungal Activity

Filamentous Fungi and Yeasts Strains and Inoculum Preparation

Filamentous fungi and yeasts strains, from clinical origin, were supplied by Microbiology Service from The Princess Hospital, Madrid. They are detailed in Table III.

TABLE III

Characteristics of the strains.

| yeast/fungus | Amphotericin B | Ketoconazole | Itraconazole | Clotrimazole | Fluconazole |
|---|---|---|---|---|---|
| C. albicans | I | S | R | S | S |
| C. glabrata | S | S | I | S | S |
| C. tropicalis | S | S | I | S | S |
| C. parapsilosis | S | S | S | S | S |
| C. lusitaniae | I | S | S | S | S |
| C. Krusei | I | S | R | S | S |
| C. guillermondii | R | R | R | R | R |
| A. fumigatus | S | S | I | S | R |
| A. niger | S | S | I | S | R |
| A. terreus | I | S | I | S | R |
| A. flavus | I | S | I | S | R |

I = intermediate activity;

S = susceptibility;

R = Resistance

Filamentous fungi and yeast cells suspensions in distilled water was prepared from a culture of 24-48 h, depending on species, in Sabouraud agar. Each suspension was adjusted to a fixed size inoculum of $1\text{-}5\times10^8$ CFU/ml with a spectrophotometer (Ferraro, M J National Committee for Clinical Laboratory Standards. 2000).

Antifungal Susceptibility Test

Antifungal susceptibility tests were developed following the standardized methodology detailed in document CLSI: M44-4: Method for Antifungal Disk diffusion susceptibility testing of yeasts consisting of disk diffusion on agar Muller-Hinton (supplemented with 2% glucose).

Figure 3:
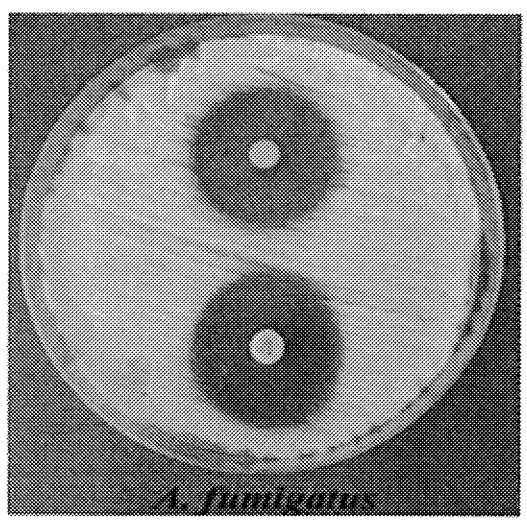
FIG. 3. Antifungal activity of the compound doxa 2 in *A. fumigatus*
Figure 4:
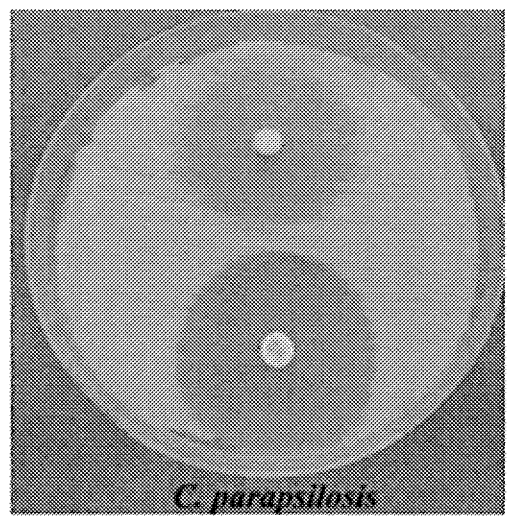
FIG. 4. Antifungal activity of the compound doxa 1 in *C. parapsilosis*.

Antifungal Activity:

The activity results are shown in Table IV. All compounds were tested at 200 μg/disc. The best activity was exhibited in yeast for DOXA 1 and in fungi for doxa 2 (Table IV and FIGS. 3 and 4).

TABLE IV

Antifungal activities detected with the compounds.

| | Activity (mm), 200 μg/disc | |
|---|---|---|
| Species | DOXA-1 | DOXA-2 |
| C. albicans | 25 | 18 |
| C. parapsilopsis | 30 | 18 |
| C. glabrata | 30 | 18 |
| C. tropicalis | 30 | 20 |
| C. lusitaniae | 38 | 20 |
| C. guilliermondii | 38 | 28 |
| A. niger | 18 | 40 |
| A. fumigatus | 15 | 30 |
| A. flavus | 20 | 38 |
| A. terreus | 18 | 40 |

Example 3—Anti-VIH Activity

Antiviral Susceptibility Test

Assessment of in vitro antiviral activity is usually performed to estimate parameters of antiviral potency and efficacy represented by the percentage of inhibition of HIV activity or IC50. The assay utilized is based on the use of recombinant viruses in which the nef gene, essential for in vitro HIV replication, has been replaced by a *Renilla* reporter gene so that viral replication can be quantified directly (Garcia-Perez J et al, J Med Virol. 2007 February; 79(2):127-37). The assay was performed infecting MT-2 cells or PHA-activated PBMCs/IL-2 with viral supernatants obtained previously. The study was development in AIDS Immunopathology Unit, National Center of Microbiology, Institute of Health Carlos III, Majadahonda, Madrid, Spain.

Viability

All assays for assessing anti-HIV activity were taken in parallel to determine cellular viability of the culture in the presence or absence of different concentrations of the isolated molecule. It was followed exactly the same methodology as in the anti-HIV assay except with the addition of complete DMEM medium instead of supernatant viral, in the same proportion, and the detection of the viability was performed with the viability detection kit CellTiter Glo (Promega), following manufacturer instructions. Viability is directly proportional to the luciferase activity obtained.

All data are expressed as percentage relative to a control with DMSO at the same concentration. Antiviral activity and toxicity curves were performed to the compound at different concentrations.

Results

Figure 5:
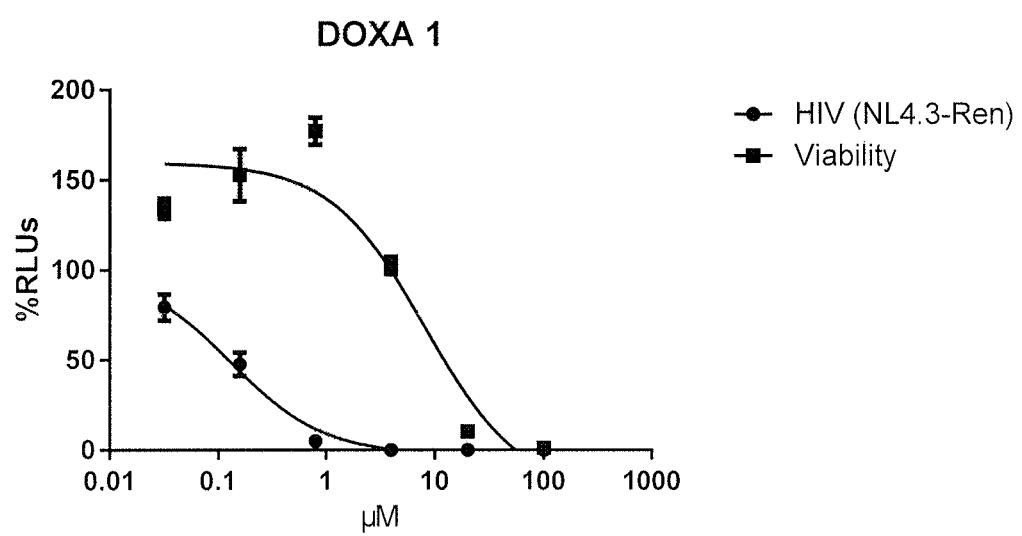
FIG. 5. Anti-VIH activity of the compound doxa 1
Figure 6:
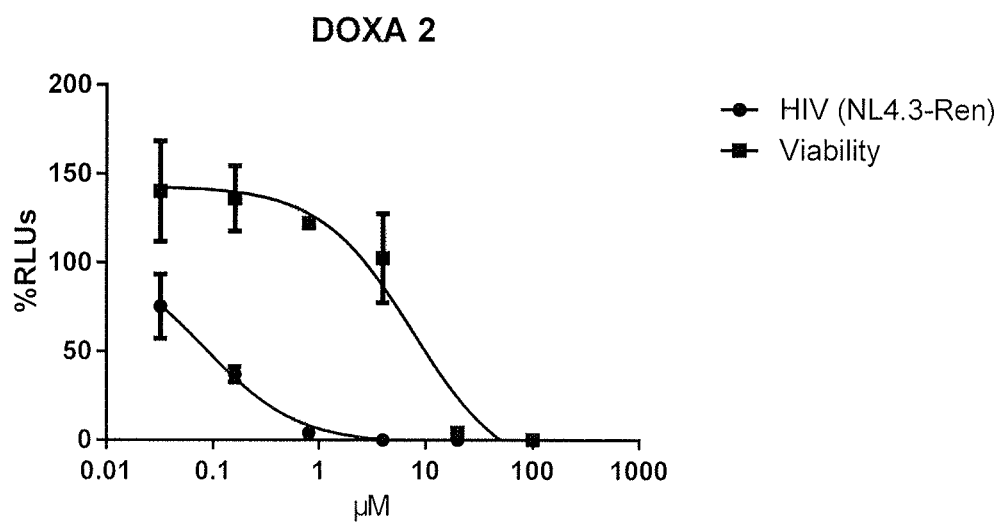
FIG. 6. Anti-VIH activity of the compound doxa 2

The profile of activity/toxicity of the compound was good with an intrinsic activity in the nanomolar range medium (FIGS. 5 and 6). The safety index values are more than 60 for DOXA 1 and about 100 for DOXA 2. DOXA 1 and DOXA 2 showed only toxicity in MT-2 cells with CC50 values of 8.203 and 7.72 μM, respectively. In addition, IC50 values are in the nanomolar range for both DOXA 1 (IC50 of 130 nM) and for DOXA 2 (IC 50 of 84 nM) (Table V).

TABLE V

IC50 (half maximal inhibitory concentration) of the compound. 95% confidence interval (CI95%). CC50 means concentration of drug required to kill 50% of cells. The value R2 is a measure of goodness-of-fit of linear regression (using graphPad prism). The best value is 1.

| | $IC_{50}$ VIH MT-2 | | | $CC_{50}$ VIH MT-2 | | |
|---|---|---|---|---|---|---|
| | μM | CI95% | $R^2$ | (μM) | CI95% | $R^2$ |
| DOXA 1 | 0.130 | 0.084 to 0.20 | 0.9757 | 8.203 | 3.64 to 18.48 | 0.9116 |
| DOXA 2 | 0.084 | 0.04 to 0.17 | 0.9482 | 7.72 | 3.15 to 18.91 | 0.9131 |

Activity tests were carried out on the virus entry with the compound. In this assay the infection was made, in parallel, with HIV virus (NL4.3-Ren) and HIV virus pseudotyped with the envelope of VSV (NL4.3-VSV-Luc). The compounds inhibited both viruses with the same potency, suggesting its activity is not dependent on virus entry.

Example 5—Antitumoral Activity

Material and Methods

For analysis of antitumor activity of the compounds an MTT assay was performed with three cell lines, detailed in Table VI. With this assay it is known if there are metabolically active cells which indicate cell survival. After incubation with the compounds the reagent Bromide reagent 3-(4,5-dimetilthiazol-2-yl)-2,5-diphenyltetrazolium was added.

TABLE VI

| | | | Mutated | | Alteration |
|---|---|---|---|---|---|
| Tumor type | Cell line | Type | genes | Mutation | in the protein |
| Breast | MCF7 | Luminal | PIK3CA | c.1633G > A | p.E545K |
| | | | BCR.A1 | c.1367T > A | p.I456T |
| Head and neck | CAL33 | Squamous | TP53 | c.524G > A | p.R175H |
| | | | PIK3CA | c.3140A > G | p.H1047R |
| | | | SMAD4 | c.766C > T | p.Q256* |
| | | | APC | c.3354T > A | p.N118K |
| Colon | HT29 | Epithelial | TP53 | c.818G > A | p.R273H |
| | | | APC | c.2557G > T | p.E853* |
| | | | PIK3CA | c.1345C > A | p.P449T |
| | | | SMAD4 | c.931C > T | p.Q311* |

Those cells that remain active convert this reagent, through SDH (succinate dehydrogenase) enzyme, to formazan. This compound has a purple hue. The more active cells are in the medium the more formazan appears and obtain more color. With subsequent absorbance reading the inventors were able to compare cultures in different times by simple statistical analysis.

Starting from an amount of 10,000 cells per well is left about 24 hours to adhere to the plate before treatment. All tests are always in triplicate. This cell line was treated at a concentration gradient from 10 nM, 50 nM, 100 nm, 250 nm, 500 nm, and 750 nM of the compound for 24, 48 and 72 hours, using as reference negative control the same line untreated.

Results

The compound DOXA-1 exhibited moderate inhibition to 750 nM, in two cell lines tested: Cal33 and HT29.

Figure 7:
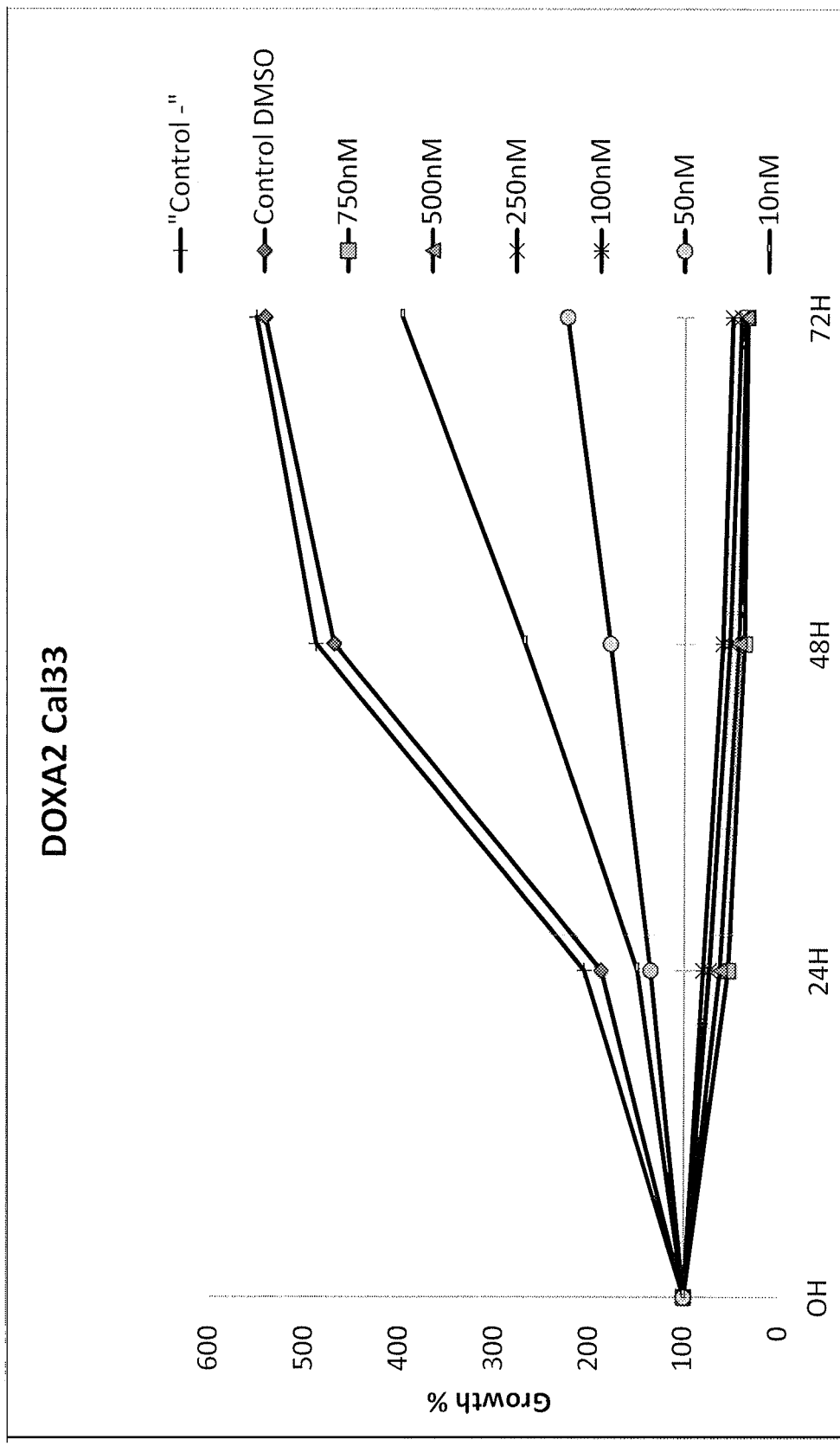
FIG. 7. Growth percentage of Cal33 cell line in the presence of various concentrations of the compound doxa 2.

The compound DOXA-2 exhibited activity in all tumor cell lines tested. The product inhibited proliferation of all cell lines although variability was observed in the optimal concentration of inhibition of viability between them. DOXA-2 inhibited to 50 nM and showed optimal inhibition to 100 nM in cell line Cal33 (FIG. 7), inhibited to 250 nM in cell line MCF7, and being the best inhibition to 50 nM in cell line HT29.

Figure 8:
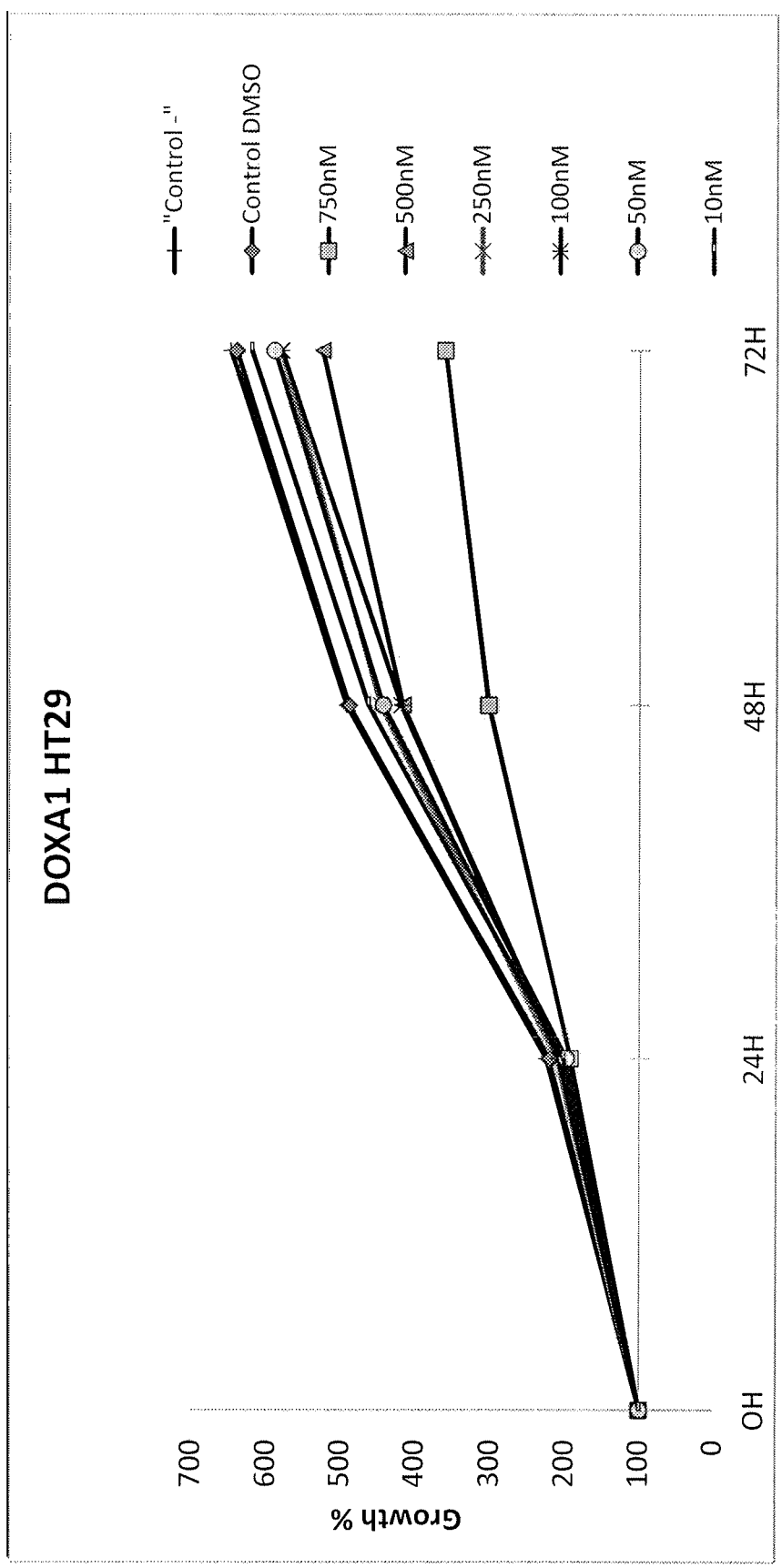
FIG. 8. Growth percentage of HT29 cell line in the presence of various concentrations of the compound doxa 1.
Figure 9:
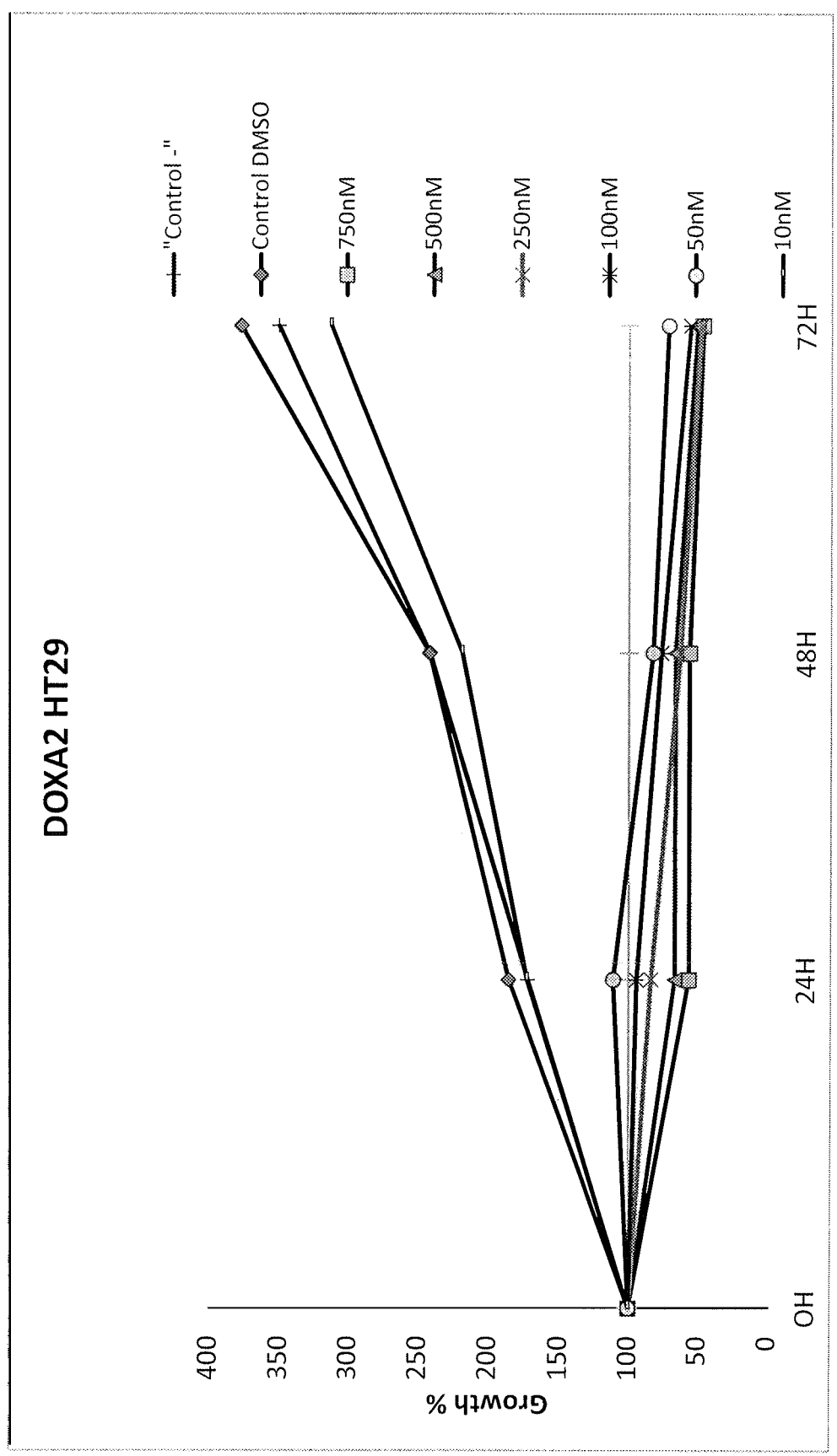
FIG. 9. Growth percentage of HT29 cell line in the presence of various concentrations of the compound doxa 2.

The FIGS. 8 and 9 show the growth percentage of the best cell line in the presence of various concentrations of the two compounds. The viability percentage was obtained by the following calculation: % viability=(DO treated cells/DO untreated cells)×100.

Untreated cells (C-) and a control incubated with solvent to the maximum concentration (C-DMSO 0.2%) were used as control of experiments.

The invention claimed is:
1. A compound of formula (I):

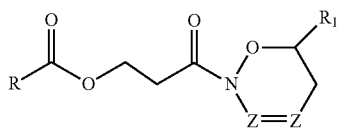

or a pharmaceutically acceptable salt, stereoisomer or solvate thereof,
wherein one Z is N and the other is —C—$R_2$; and $R_2$ and $R_1$ are independently selected from the group consisting of H, alkyl and aryl, and wherein P is selected from the group consisting of
a) a linear or branched $C_{1-8}$ alkyl, a linear or branched $C_{2-8}$ alkenyl, di-halo methyl, tri-halo methyl, $C_{3-6}$ cycloalkyl, ($C_{1-4}$ alkyl)O—$CH_2$—, or amine di-substituted with independently selected $C_{1-6}$ alkyl groups,
b) phenyl optionally substituted with one or more groups independently selected from the group consisting of $C_{1-8}$ alkyl, $C_{2-8}$ alkenyl, halogen, phenyl, $C_{1-6}$ alkoxy, amine di-substituted with independently selected $C_{1-6}$ alkyl groups, —NHC(O)$R_3$—, —C(O)NH—$R_3$, —OC(O)$R_3$, and —C(O)O$R_3$—, wherein $R_3$ is $C_{1-6}$ alkyl,
c) a 5-6 membered aromatic ring having one or more heteroatoms selected from the group consisting of N, S, and O and being optionally substituted with one or more groups independently selected from the group consisting of:
   $C_{1-8}$ alkyl, linear or branched $C_{2-8}$ alkenyl, $C_{5-6}$ cycloalkyl
   phenyl as defined in b),
   5-6 membered aromatic ring group,
   halogen,
   ($C_{1-6}$alkyl)O$CH_2$—, $C_{1-6}$ alkoxy,
   amino di-substituted with $C_{1-6}$ alkyl groups,
   NHC(O)$R_3$—, —C(O)NH—$R_3$, —OC(O)$R_3$, and —C(O)O$R_3$—, wherein $R_3$ is $C_{1-6}$ alkyl,
d) a bicyclic ring containing at least one phenyl group and a $C_{5-6}$ aromatic heterocyclic group having one or more heteroatoms selected from the group consisting of N, S, and O, wherein the phenyl group of said bicyclic ring is optionally substituted with one or more groups independently selected from the group consisting of
   $C_{1-6}$ alkyl, linear or branched $C_{2-8}$ alkenyl, $C_{5-6}$ cycloalkyl
   phenyl as defined in b),
   5-6 membered aromatic ring group,
   halogen,
   ($C_{1-6}$alkyl)O$CH_2$—, $C_{1-6}$; alkoxy,
   amino di-substituted with $C_{1-6}$alkyl groups,
   NHC(O)$R_3$—, —C(O)NH—$R_3$, —OC(O)$R_3$, and —C(O)O$R_3$—, wherein $R_3$ is $C_{1-6}$ alkyl, and
e) —CH($R_4$)—CH($R_5$)COOH, wherein $R_4$ is selected from the group consisting of H, $NH_2$, OH and $CH_2$COOH, and wherein $R_5$ is selected from the group consisting of H, $NH_2$, OH and $CH_2$COOH.

2. The compound according to claim 1 having formula:

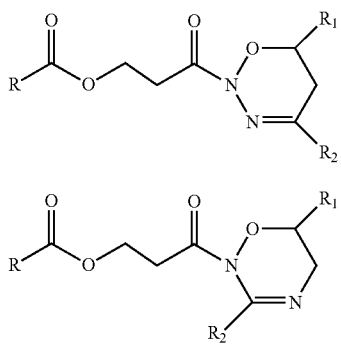

or a pharmaceutically acceptable salt, stereoisomer or solvate thereof.

3. The compound according to claim 1 wherein $R_1$ and $R_2$ are the same group, or a pharmaceutically acceptable salt, stereoisomer or solvate thereof.

4. The compound according to claim 1, wherein $R_1$ and $R_2$ are —$(CH_2)_4$—$CH_3$, or a pharmaceutically acceptable salt, stereoisomer or solvate thereof.

5. The compound according to claim 1 having formula:

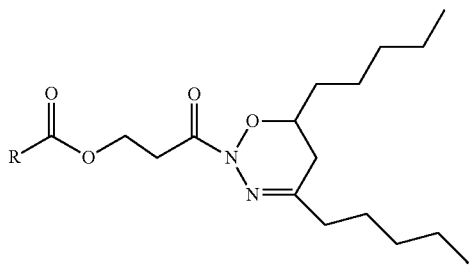

or a pharmaceutically acceptable salt, stereoisomer or solvate thereof.

6. The compound according to claim 1, wherein R is a methyl group or —$(CH_2)_2$—COOH, or a pharmaceutically acceptable salt, stereoisomer or solvate thereof.

7. A method for preparing a compound of formula (I) according to claim 1 or a pharmaceutically acceptable salt, stereoisomer or solvate thereof, comprising reacting a compound of formula (X) in the presence of triethylamine and an organic solvent:

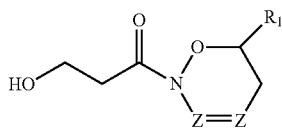

wherein Z and R1 are defined according to claim 1, with a compound of formula (XI):

wherein X is an halogen or —(O)C(O)R, wherein R is selected according to claim 1, or reacting the compound of formula (X) with a compound of formula (XII):

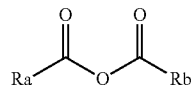

wherein Ra and Rb together form, with the anhydride group C(O)OC(O) to which they are attached, a substituted or unsubstituted cyclic group.

8. A pharmaceutical composition comprising a compound according to claim 1 and a pharmaceutically acceptable excipient.

9. A method for the treatment of an infection caused by a bacterium, fungus or virus in a subject in need thereof or for the treatment of cancer in a subject in need thereof comprising the administration of a compound as defined in claim 1, wherein the cancer is selected from the group consisting of breast cancer, biliary tract cancer, bladder cancer, brain cancer, cervical cancer, head and neck carcinoma, choriocarcinoma colon cancer, colorectal cancer, endometrial cancer, esophageal cancer, gastric cancer, hematological neoplasms, T-cell acute lymphoblastic leukemia/lymphoma hairy cell leukemia, chronic myelogenous leukemia, multiple myeloma, AIDS-associated leukemias, adult T-cell leukemia/lymphoma, intraepithelial neoplasms, liver cancer, hepatoma, lung cancer, pleural mesothelioma, lymphomas neuroblastomas, oral cancer parotid gland cancer, ovarian cancer, pancreatic cancer, prostate cancer, kidney cancer, suprarenal cancer, rectal cancer, sarcomas, skin cancer, cervix cancer, testicular cancer, thyroid cancer, and renal cancer.

10. The method according to claim 9 wherein the bacterium is a Gram positive bacterium or a Gram-negative bacterium.

11. The method according to claim 10, wherein the Gram positive bacterium is from phylum Actinobacteria or from phylum Firmicutes or wherein the Gram negative bacterium is from phylum proteobacteria.

12. The method according to claim 11 wherein the bacterium from phylum Actinobacteria is a bacterium from genus *Nocardia, Tsukamurella* or *Mycobacterium* and/or the bacterium from phylum Firmicutes is a bacterium from genus *Staphylococcus, Bacillus* or *Enterococcus*.

13. The method according to claim 11 wherein the bacterium from phylum proteobacteria is from genus *Acinetobacter, Pseudomonas* or *Escherichia*.

14. The method according to claim 12 wherein the bacterium from the genus *Nocardia* is *N. carnea* or *N. cyriacigeorgica*, the bacterium from genus *Tsukamurella* is *T. pulmonis*, the bacterium from genus *Mycobacterium* is *M. chelonae, M. abscessus* or *M. fortuitum*, the bacterium from genus *Staphylococcus* is *S. aureus* or *S. epidermidis*, the bacterium from genus *Bacillus* is *B. cereus*, the bacterium from genus *Enterococcus* is *E. faecium* or *E. faecalis*.

15. The method according to claim 13 wherein the bacterium from genus *Acinetobacter* is *A. baumannii*, the bacterium from genus *Pseudomonas* is *P. aeruginosa* and/or the bacterium from genus *Escherichia* is *E. coli*.

16. The method according to claim 9 wherein the fungi is selected from genus *Candida* or *Aspergillus*.

17. The method according to claim 16 wherein the fungus from genus *Candida* is *C. albicans, C. parapsilopsis, C. glabrata, C. tropicalis, C. lusitaniae* or *C. guilliermondi* and the fungus from genus *Aspergillus* is *A. fumigatus, A. flavus, A. niger* or *A. terreus*.

18. The method according to claim 9 wherein the virus is selected from HIV, herpes simplex I, herpes simplex II, Suid herpesvirus 1 and Equine herpesvirus 1.

19. The method according to claim 9 wherein the cancer is selected from the group consisting of breast, head and neck, colon, prostate, lung, cervix, and pancreatic cancer, glioblastoma and osteosarcoma.

\* \* \* \* \*